(12) United States Patent
Holman et al.

(10) Patent No.: US 8,444,686 B2
(45) Date of Patent: May 21, 2013

(54) CATHETER WITH REMOVABLE BALLOON PROTECTOR AND STENT DELIVERY SYSTEM WITH REMOVABLE STENT PROTECTOR

(75) Inventors: Thomas J. Holman, Minneapolis, MN (US); Louis G. Ellis, St. Anthony, MN (US); Gregory K. Olson, Elk River, MN (US); Linda R. Lorentzen-Cornelius, Wayzata, MN (US); Richard J. Traxler, Minneapolis, MN (US); Scott M. Hanson, Columbia Heights, MN (US); Tracee E. J. Eidenschink, Wayzata, MN (US); Sonja J. K. Williams, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 332 days.

(21) Appl. No.: 12/620,368

(22) Filed: Nov. 17, 2009

(65) Prior Publication Data
US 2010/0069839 A1    Mar. 18, 2010

Related U.S. Application Data

(60) Continuation of application No. 09/737,118, filed on Dec. 14, 2000, now Pat. No. 7,618,398, which is a continuation of application No. 09/528,613, filed on Mar. 20, 2000, now Pat. No. 6,416,529, which is a division of application No. 09/034,434, filed on Mar. 4, 1998, now Pat. No. 6,152,944, which is a continuation-in-part of application No. 08/812,351, filed on Mar. 5, 1997, now Pat. No. 5,893,868.

(51) Int. Cl.
*A61F 2/06* (2006.01)

(52) U.S. Cl.
USPC .................................................. 623/1.11

(58) Field of Classification Search
USPC .............. 623/1.11, 1.22, 1.23, 23.64, 23.65, 623/23.66; 606/108, 192, 194, 198; 604/96.01, 604/103.05, 104, 160–162, 509
See application file for complete search history.

(56) References Cited

U.S. PATENT DOCUMENTS

| | | | |
|---|---|---|---|
| 4,649,922 A | 3/1987 | Wiktor | |
| 4,710,181 A | 12/1987 | Fuqua | |
| 4,733,665 A | 3/1988 | Palmaz | |
| 4,740,207 A | 4/1988 | Kreamer | |
| 4,921,479 A * | 5/1990 | Grayzel | 604/509 |
| 4,950,227 A | 8/1990 | Savin et al. | |
| 5,007,926 A | 4/1991 | Derbyshire | |

(Continued)

FOREIGN PATENT DOCUMENTS

| | | |
|---|---|---|
| EP | 0461474 B1 | 7/1994 |
| EP | 0707837 A1 | 4/1996 |

(Continued)

*Primary Examiner* — Melanie Tyson
(74) *Attorney, Agent, or Firm* — Vidas, Arrett & Steinkraus, P.A.

(57) ABSTRACT

A medical device has a catheter with a proximal portion, a distal portion, a shaft and an expandable member located at the distal portion. The expandable member is constructed and arranged for expanding the outer diameter of the catheter from a contracted state to an expanded state. A removable sleeve is positioned around the entire length of the expandable member. The sleeve has a first end and a second end, and an inner diameter that increases over the entire length of the sleeve.

4 Claims, 18 Drawing Sheets

U.S. PATENT DOCUMENTS

| | | | |
|---|---|---|---|
| 5,015,231 A | 5/1991 | Keith et al. | |
| 5,053,007 A | 10/1991 | Euteneuer | |
| 5,066,282 A | 11/1991 | Wijay et al. | |
| 5,137,512 A | 8/1992 | Burns et al. | |
| 5,163,952 A | 11/1992 | Friox | |
| 5,211,654 A * | 5/1993 | Kaltenbach | 606/191 |
| 5,282,786 A | 2/1994 | Ureche | |
| 5,290,306 A | 3/1994 | Trotta et al. | |
| 5,306,286 A | 4/1994 | Stack et al. | |
| 5,342,307 A * | 8/1994 | Euteneuer et al. | 604/103 |
| 5,352,236 A | 10/1994 | Jung et al. | |
| 5,417,707 A | 5/1995 | Parkola | |
| 5,425,710 A | 6/1995 | Khair et al. | |
| 5,445,646 A | 8/1995 | Euteneuer et al. | |
| 5,527,292 A | 6/1996 | Adams et al. | |
| 5,540,701 A | 7/1996 | Sharkey et al. | |
| 5,545,209 A | 8/1996 | Roberts et al. | |
| 5,556,383 A | 9/1996 | Wang et al. | |
| 5,569,294 A | 10/1996 | Parkola | |
| 5,584,852 A | 12/1996 | Parkola | |
| 5,690,644 A | 11/1997 | Yurek et al. | |
| 5,723,004 A | 3/1998 | Dereume et al. | |
| 5,735,859 A | 4/1998 | Fischell et al. | |
| 5,749,852 A | 5/1998 | Schwab et al. | |
| 5,765,682 A | 6/1998 | Bley et al. | |
| 5,766,203 A | 6/1998 | Imran et al. | |
| 5,868,707 A | 2/1999 | Williams et al. | |
| 5,893,868 A * | 4/1999 | Hanson et al. | 623/1.11 |
| 5,908,448 A | 6/1999 | Roberts et al. | |
| 5,911,752 A * | 6/1999 | Dustrude et al. | 623/1.1 |
| 6,132,450 A * | 10/2000 | Hanson et al. | 606/198 |
| 6,152,944 A * | 11/2000 | Holman et al. | 623/1.11 |
| 6,203,508 B1 | 3/2001 | Ren et al. | |
| 6,283,743 B1 | 9/2001 | Traxler et al. | |
| 6,416,529 B1 * | 7/2002 | Holman et al. | 606/194 |
| 6,991,639 B2 * | 1/2006 | Holman et al. | 606/194 |

FOREIGN PATENT DOCUMENTS

| | | |
|---|---|---|
| EP | 0553960 B1 | 8/1997 |
| GB | 2179258 | 3/1987 |
| WO | 95/11718 | 5/1995 |
| WO | 96/08286 A1 | 3/1996 |

* cited by examiner

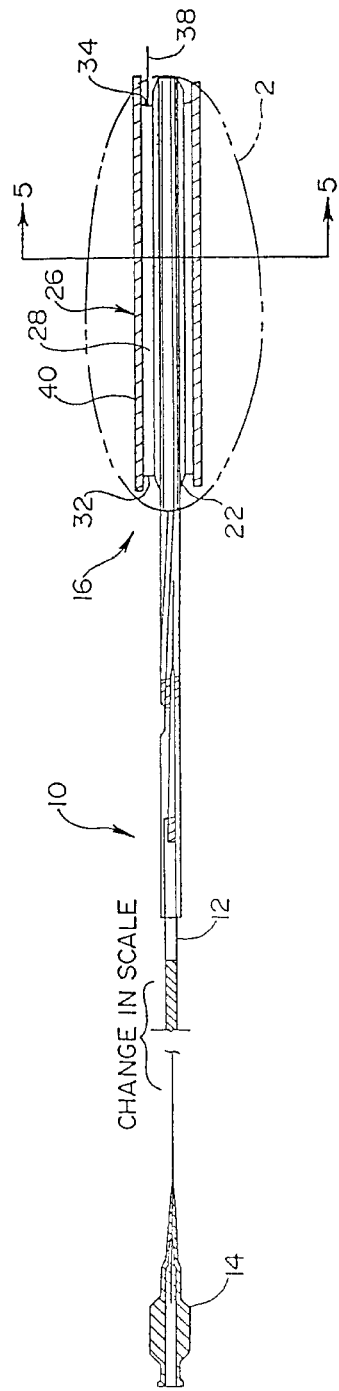
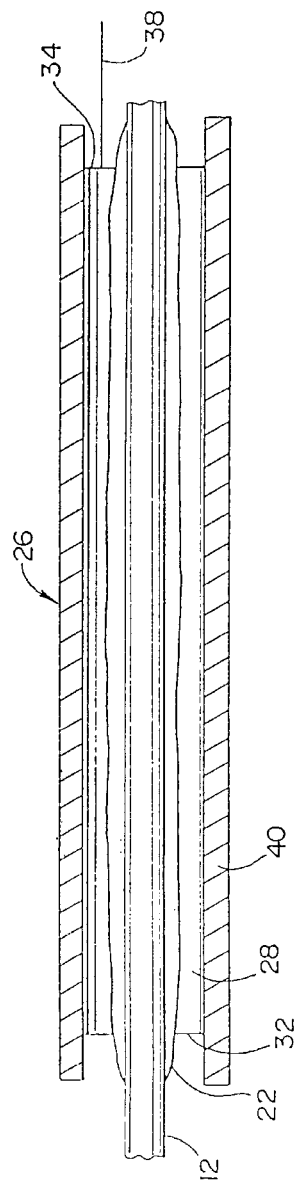

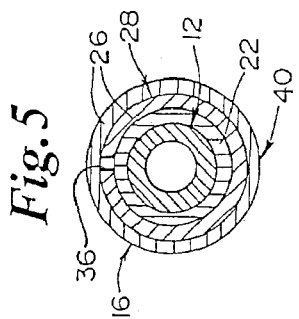
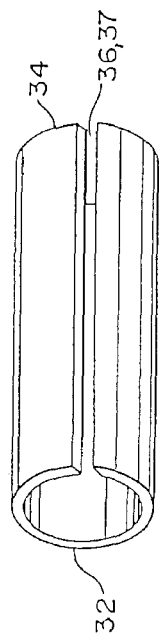
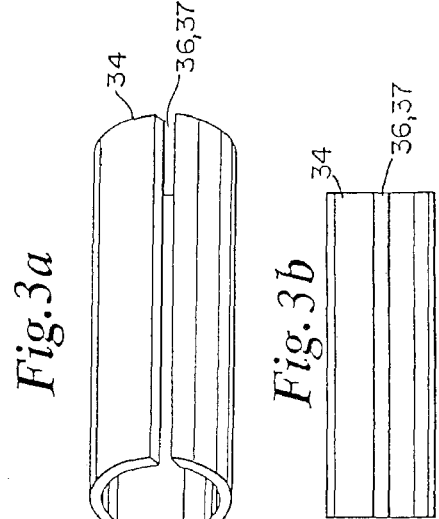
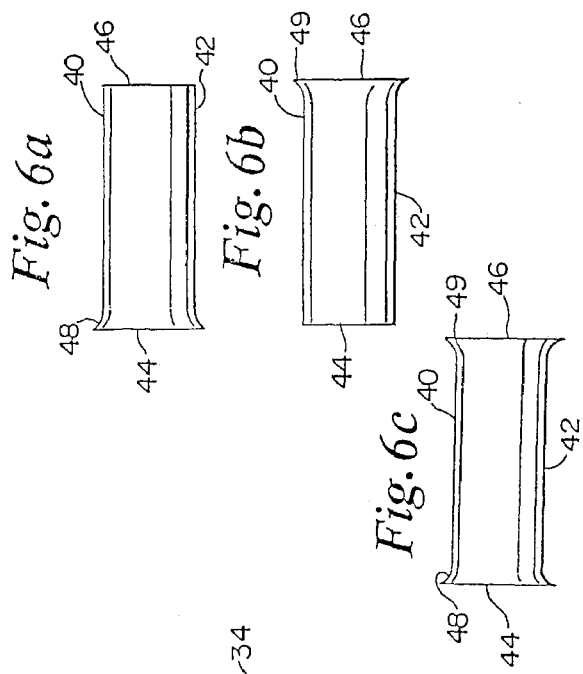
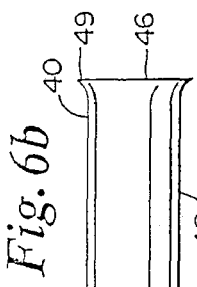
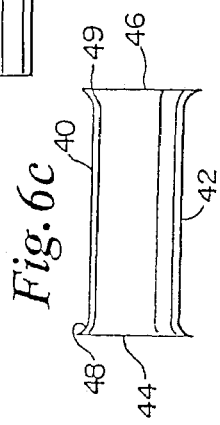
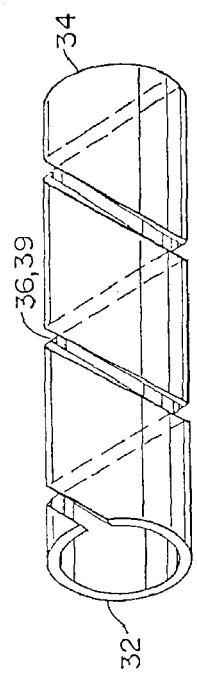
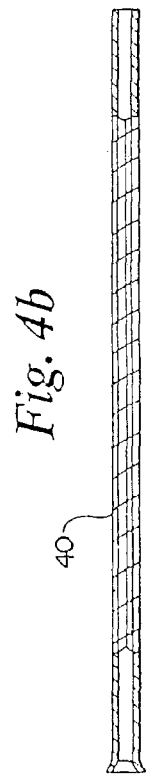
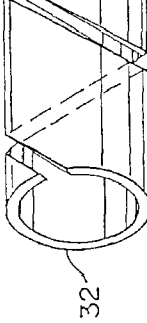

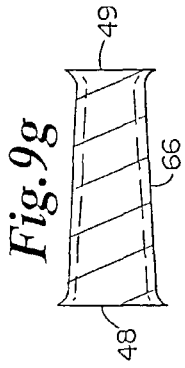
Fig.9g
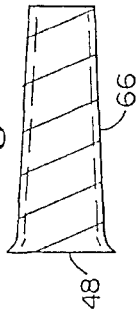
Fig.9h
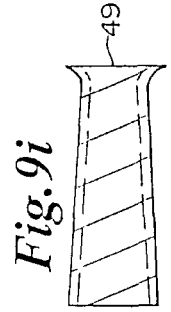
Fig.9i
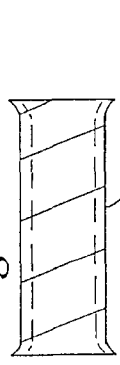
Fig.9c
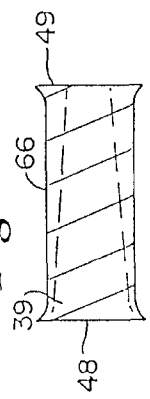
Fig.9d
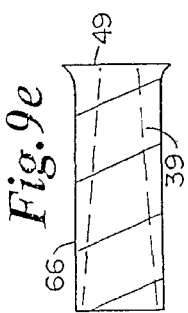
Fig.9e
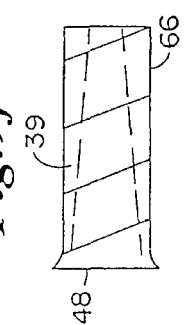
Fig.9f
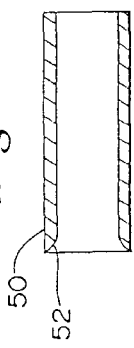
Fig.7  Fig.8  Fig.9a
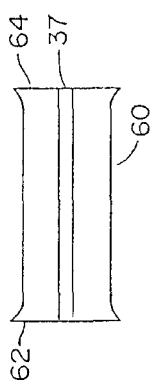
Fig.9b
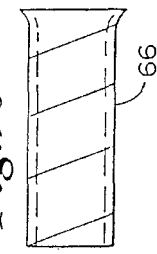

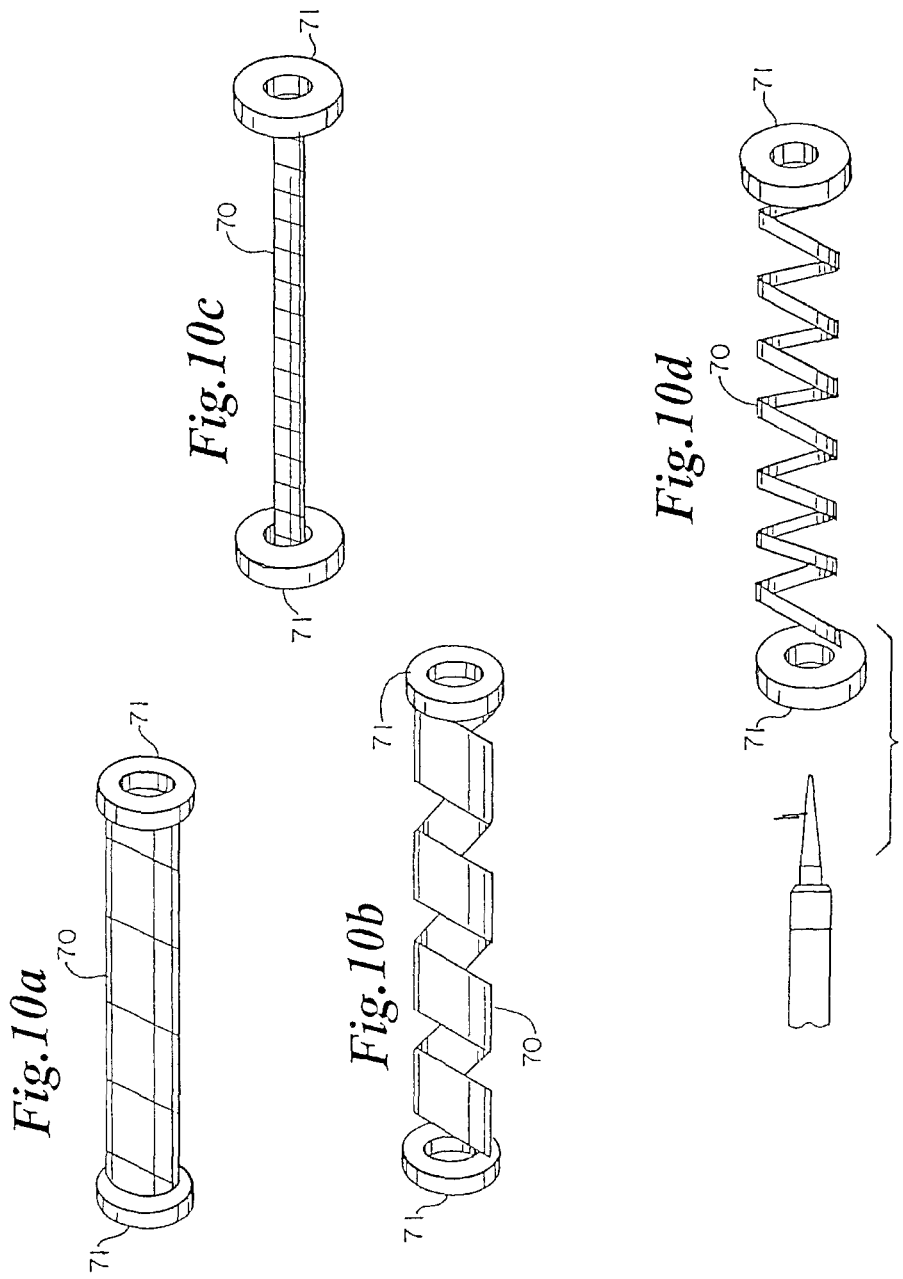

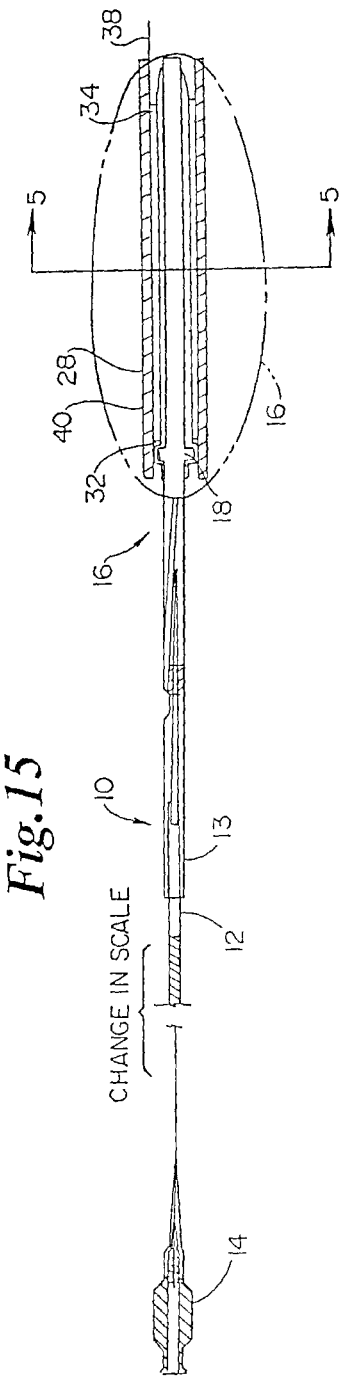
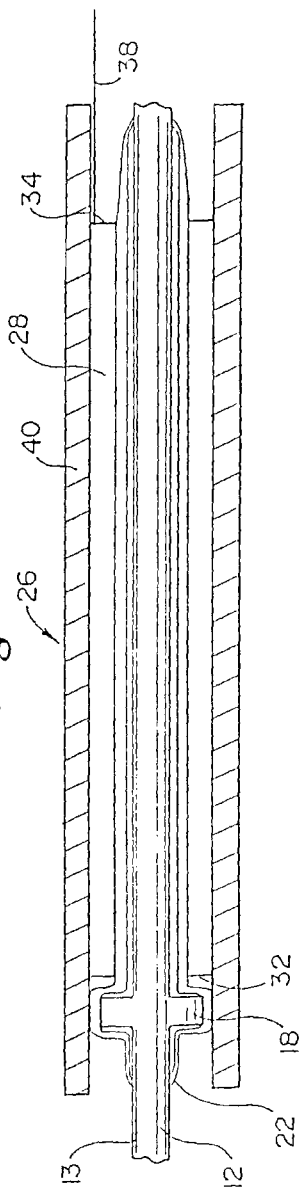
Fig.15
Fig.16

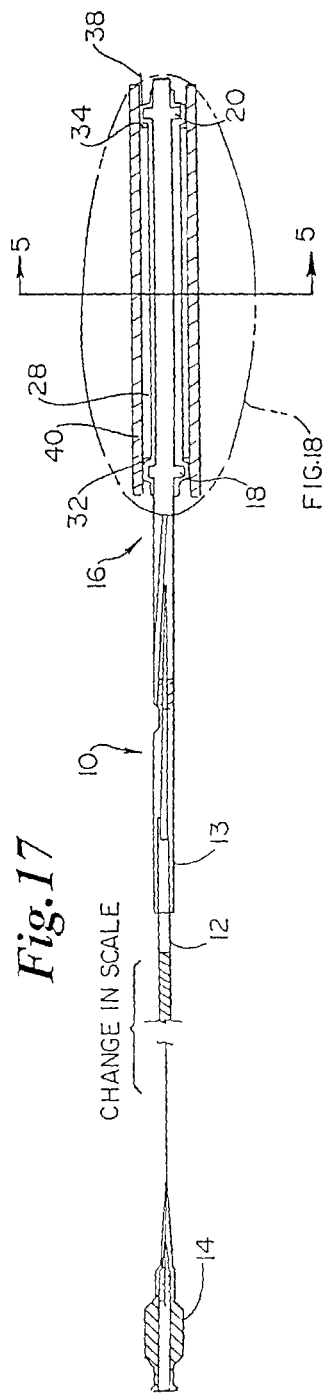
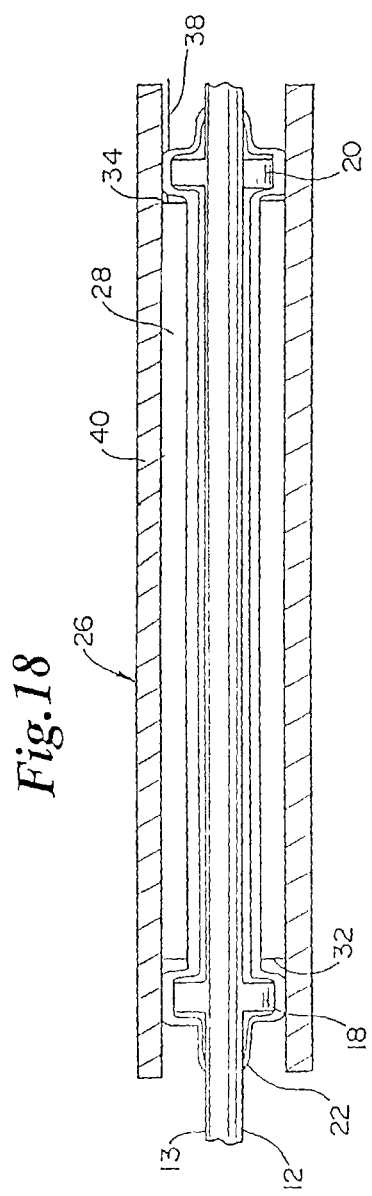
Fig.17
Fig.18

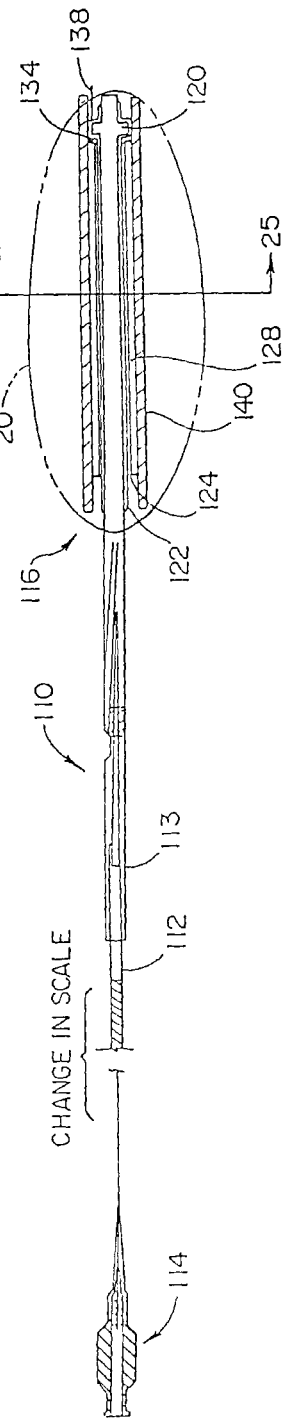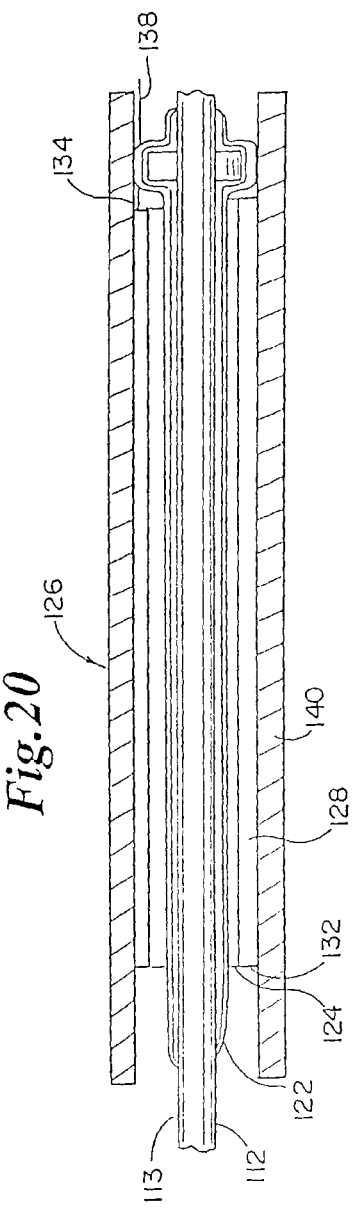

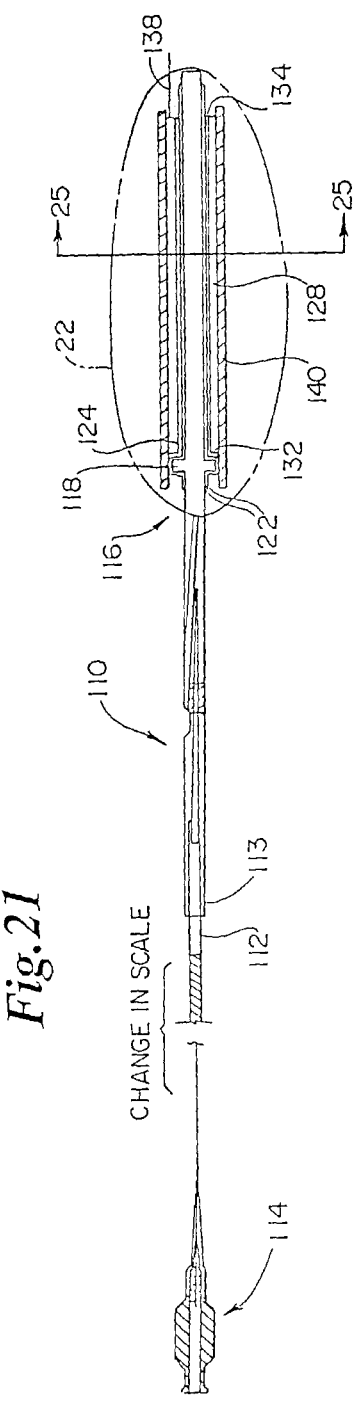
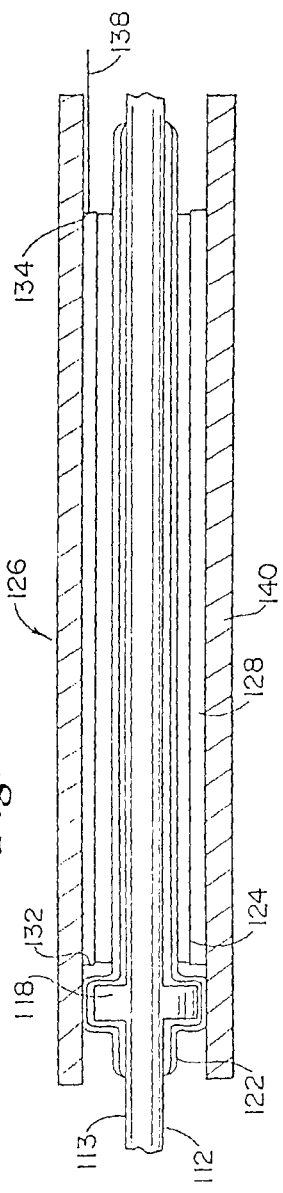
Fig.21
Fig.22

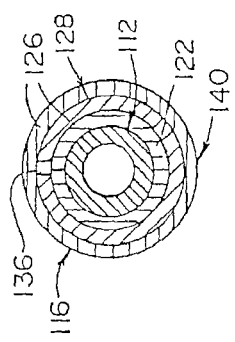
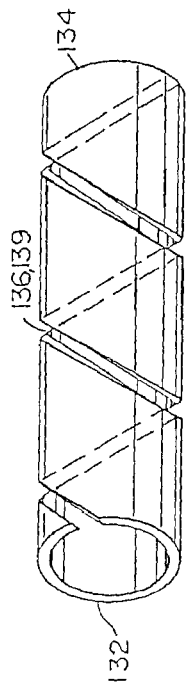
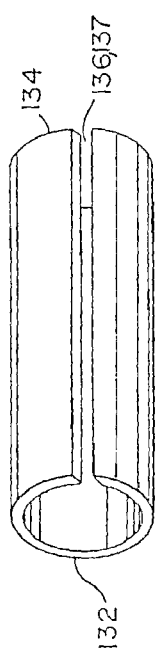
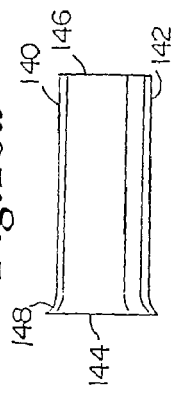
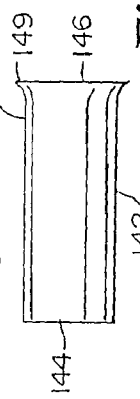
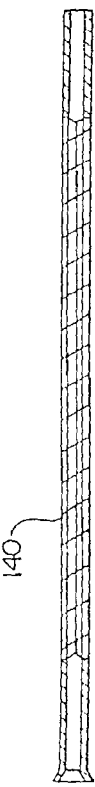
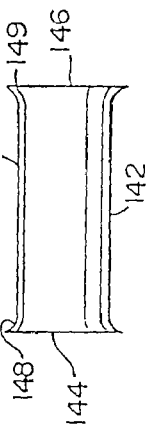

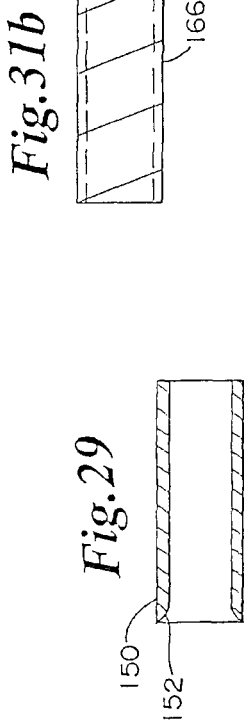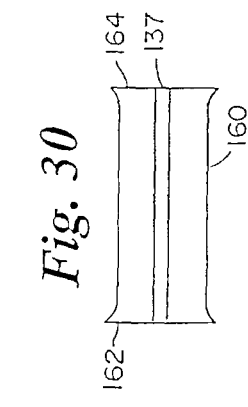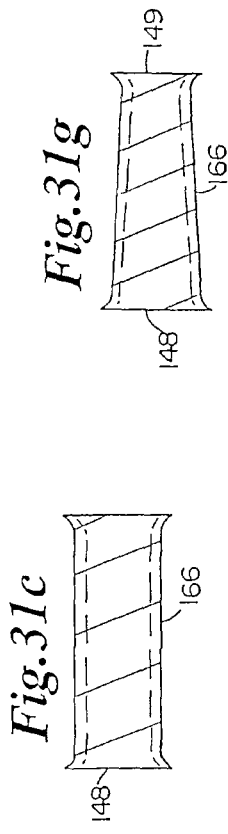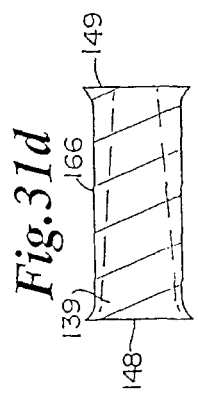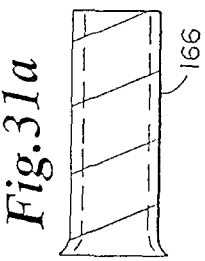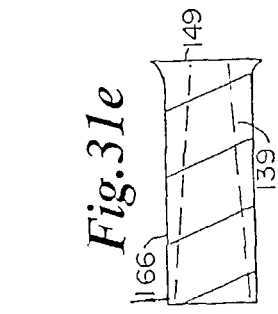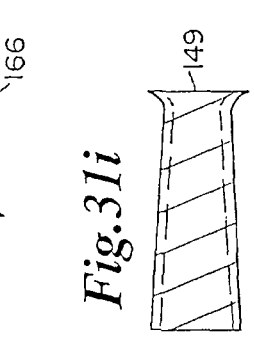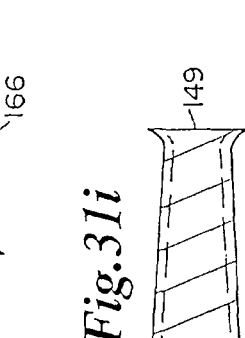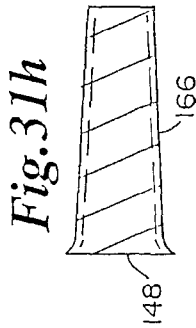

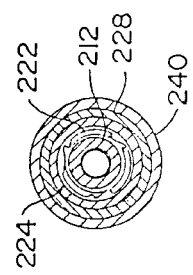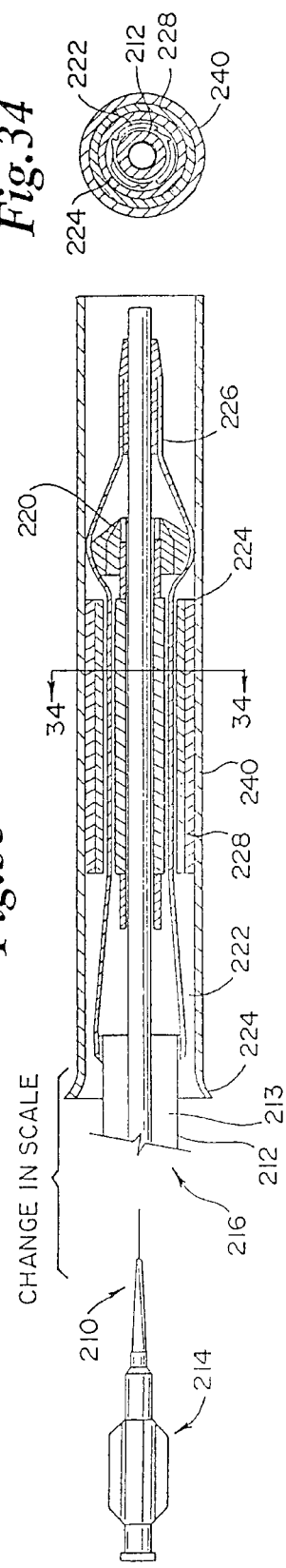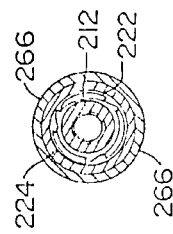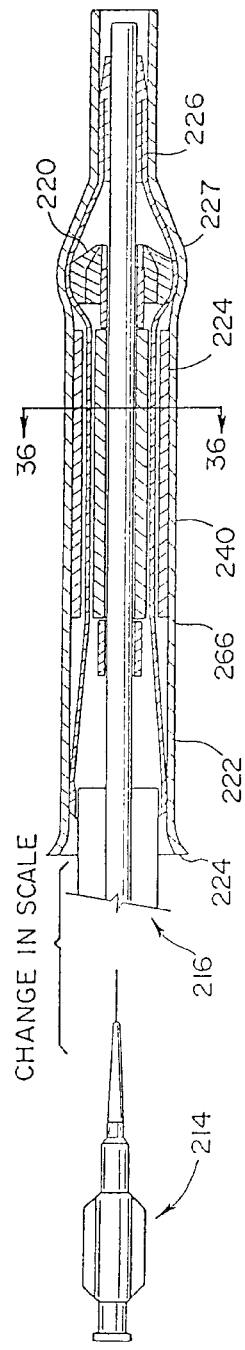

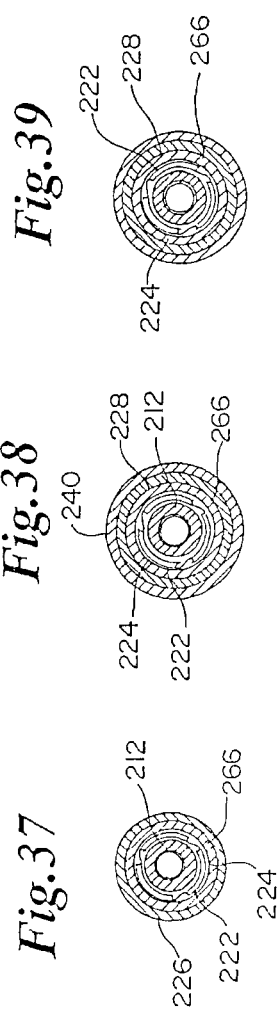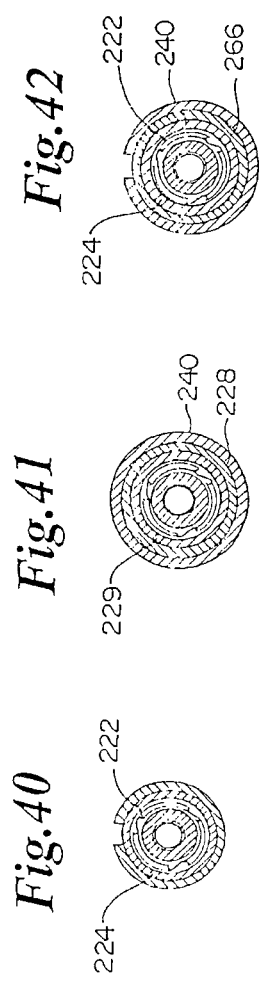

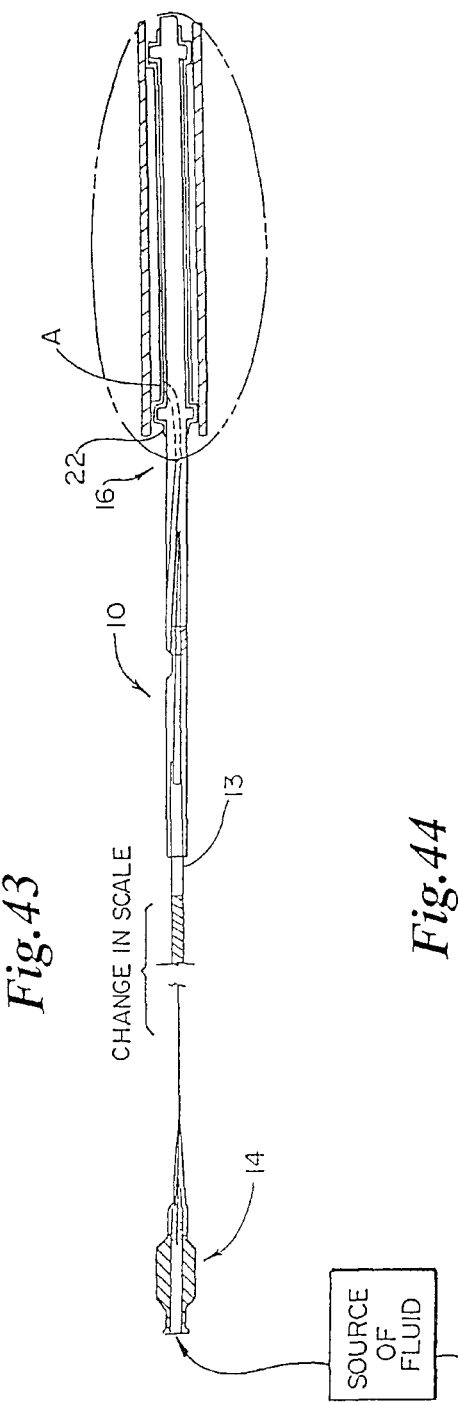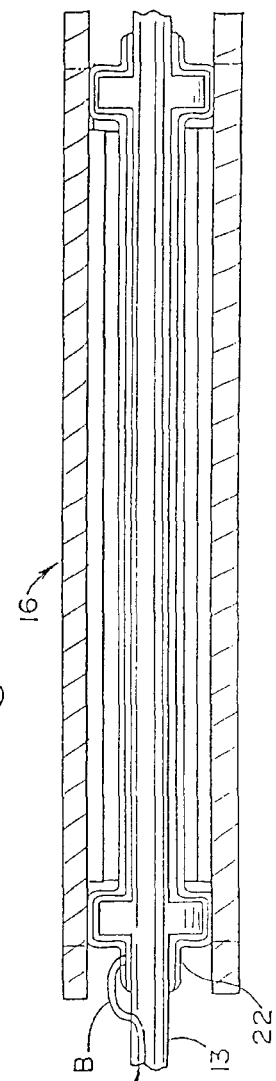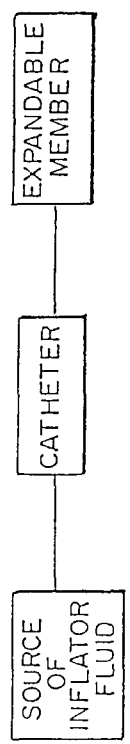
Fig.43
Fig.44
Fig.45

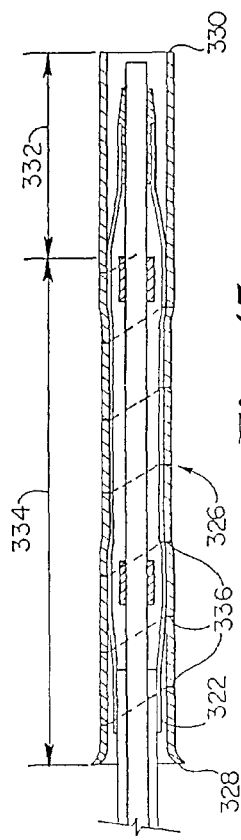
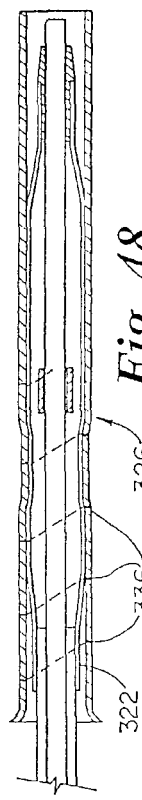
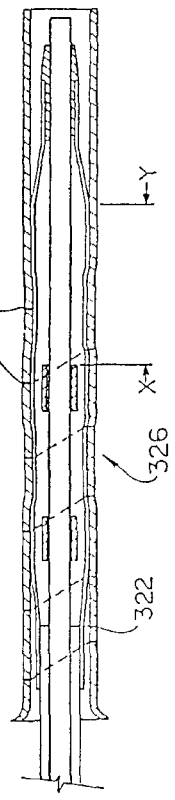
Fig. 46
Fig. 47
Fig. 48

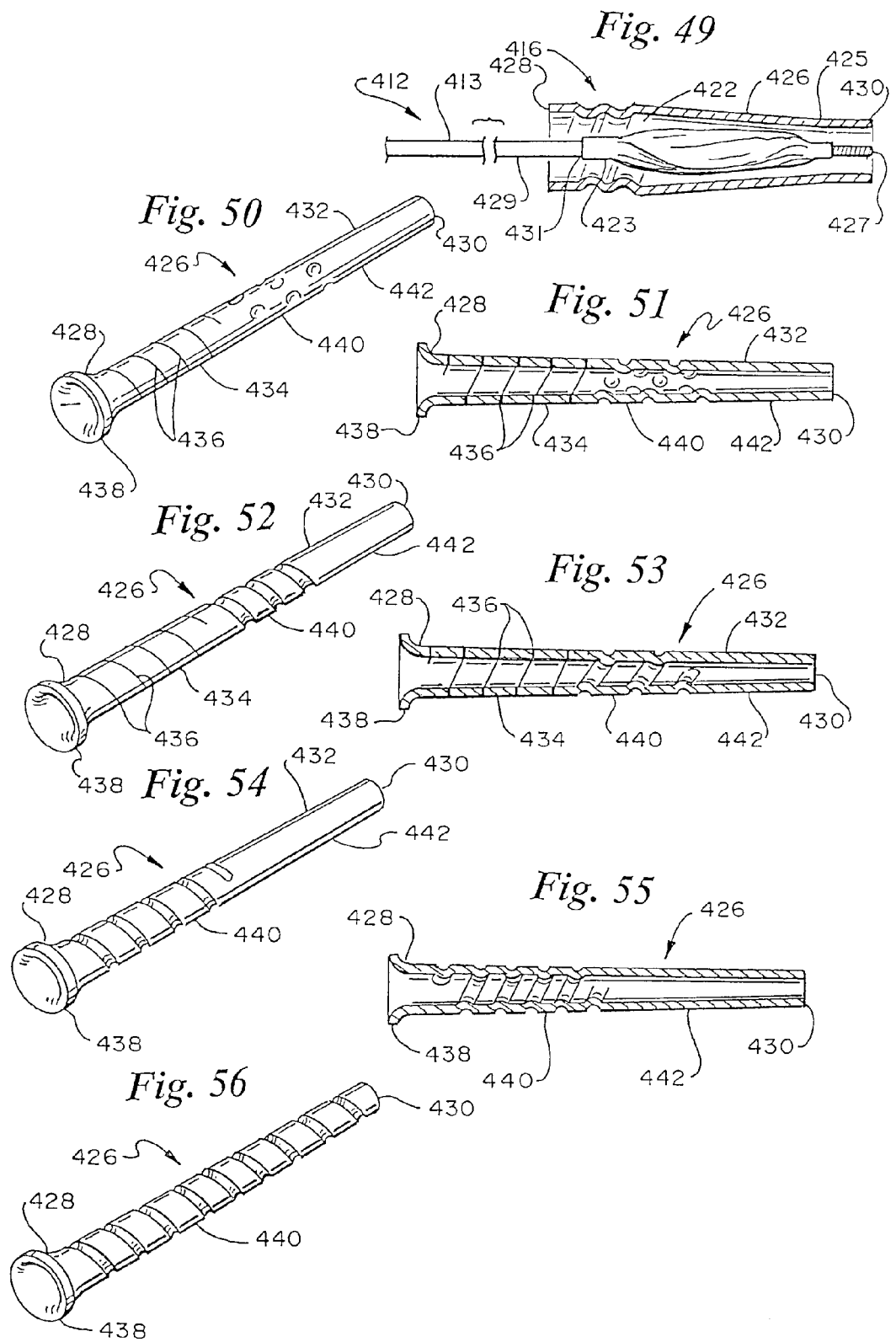

CATHETER WITH REMOVABLE BALLOON PROTECTOR AND STENT DELIVERY SYSTEM WITH REMOVABLE STENT PROTECTOR

CROSS REFERENCE TO RELATED APPLICATIONS

This application is a continuation of Ser. No. 09/737,118, filed Dec. 14, 2000 now U.S. Pat. No. 7,618,398 which is a continuation of Ser. No. 09/528,613, filed on Mar. 20, 2000 now U.S. Pat. No. 6,416,529 which is a division of Ser. No. 09/034,434, filed Mar. 4, 1998, now U.S. Pat. No. 6,152,944, which is a Continuation in part continuation-in-part of U.S. patent application Ser. No. 08/812,351, filed Mar. 5, 1997, now U.S. Pat. No. 5,893,868, incorporated herein by reference.

BACKGROUND OF THE INVENTION

1. Field of the Invention

The present invention relates generally to catheters having an expandable balloon and to premounted balloon expandable stent balloon catheters, and specifically to a dilatation balloon catheter with a balloon protector means or a stent delivery system with a balloon and stent protector means.

2. Description of Related Art

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter. In typical PTCA procedures, the cardiovascular system of a patient is accessed with an introducer, usually in the groin area. All other devices including a guiding catheter are percutaneously introduced into the cardiovascular system of a patient through the introducer and advanced through a vessel until the distal end thereof is at a desired location in the vasculature. A guide wire and a dilatation catheter having a balloon on the distal end thereof are introduced through the guiding catheter with the guide wire sliding through the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with a fluid at relatively high pressures, such as greater than about four atmospheres, to radially compress the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, called a stent, inside the artery at the lesion. In general, stents are prosthetic devices which can be positioned within a body cavity, for example, a blood vessel of the body of a living human or in some other difficulty accessible place. A stent generally has a diameter which may be increased or decreased. Stents are particularly useful for permanently widening a vessel which is in a narrowed state, or for internally supporting a vessel damaged by an aneurysm.

Such stents are typically introduced into the body cavity by use of a catheter. The catheter is usually of the balloon catheter type in which the balloon is utilized to expand the stent, which is positioned over the balloon, to place it in a selected location in the body cavity. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Dreamer and U.S. Pat. No. 5,007,926 to Derbyshire.

One important characteristic of a dilatation balloon catheter is its "profile", which is determined by the outer diameter (O.D.) of the distal end portion of the balloon and stent when deflated. The outer diameter affects the ease and ability of the dilatation catheter to pass through a guide catheter, through the coronary arteries, and across a tight lesion. Considerable effort has been made in developing low profile dilatation balloon catheters. U.S. Pat. No. 5,342,307, incorporated herein by reference, discloses a balloon protector sleeve used with a tri-fold dilatation balloon catheter for angioplasty.

Minimization of "profile" is of importance in balloon catheters and stent delivery systems. Accordingly, the present invention is particularly directed to improved arrangements of balloon catheters having a balloon protector and stent delivery systems having a balloon and including a stent protector means which provide a minimized profile.

SUMMARY OF THE INVENTION

This invention concerns medical devices such as balloon catheters and apparatus suitable for delivery of stents to body cavities. The present invention is particularly directed to improved balloon protectors for use with balloon catheters and to improved arrangements for stent delivery systems, the improvements comprising stent protector means.

Accordingly, the present invention provides a catheter having an expandable distal portion constructed and arranged for expanding the outer diameter of the catheter from a contracted state to an expanded state. The distal portion of the catheter comprises a balloon which is folded or otherwise collapsed, and is expandable to an expanded condition. The balloon protector may comprise removable first and second sleeves. The first removable (inner) sleeve is positioned around the balloon, the inner sleeve being made of a lubricious material and further comprising a first end, a second end and a slit extending therethrough. The slit may extend from end to end. Alternatively, the slit may extend along a predetermined length of the sleeve, the rest of the length of the sleeve comprising a continuous tube. The slit provides a variable inner diameter to ease sliding the sleeve over the balloon. The second removable (outer) sleeve is positioned over the first (inner) sleeve, the outer sleeve having a constrictive relationship with the inner sleeve. The outer sleeve thereby provides an additional compressive force to reduce the profile of the constricted balloon. For example, the outer sleeve may have an inner diameter less than the outer diameter of the inner sleeve, whereby when compressed by the outer sleeve, the inner sleeve will have an inner diameter approximately equal to or greater than the profile of the balloon in its contracted state. The inner and outer sleeves are removed prior to use of the catheter.

Alternatively, the balloon protector means may comprise a single compressive sleeve. This single compressive sleeve may be of any configuration described herein. A preferred embodiment of the single sleeve has a slit along the length thereof. Another preferred embodiment of the single sleeve has a helical slit along a predetermined length of the sleeve, defining a spiral cut region and a continuous tubular region. Yet another preferred embodiment has a spiral cut region and a continuous tubular region, the continuous tubular region comprising a dimpled region and a straight tubular region. The dimples may be round-like, spiral, triangular, oval, oblong, circular (like tire treads) around the circumference or at an angle around the circumference, or combinations thereof. The dimples may also be of any other suitable configuration. In another alternative embodiment, the single sleeve may comprise a dimpled region extending along part of the single sleeve or the entire sleeve.

The present invention also provides a catheter having an expandable distal portion constructed and arranged for expanding the outer diameter of the catheter from a contracted state to an expanded state. The distal portion of the catheter may further comprise one or two dams (also referred to as enlarged portions, stops, bumpers, longitudinal motion preventers, or the like) and a balloon. The balloon is folded or otherwise collapsed, and is expandable to an expanded condition. The catheter further comprises a balloon protector means comprising removable first and second sleeves. The first removable (inner) sleeve is positioned over the balloon and between the dams (where two dams are present), the inner sleeve being made of a lubricious material and further comprising a first end, a second end and a slit extending therethrough. The slit may extend from end to end. Alternatively, the slit may extend along a predetermined length of the sleeve, the rest of the length of the sleeve comprising a continuous tube. The continuous tube may further comprise a dimpled region and a straight tubular region. The slit provides a variable inner diameter to ease sliding the sleeve over the balloon. The second removable (outer) sleeve is positioned over the first sleeve and dams, the outer sleeve having a constrictive relationship with the inner sleeve. The outer sleeve thereby provides an additional compressive force to reduce the profile of the collapsed balloon. For example, the outer sleeve may have an inner diameter less than the outer diameter of the inner sleeve, whereby when compressed by the outer sleeve, the inner sleeve will have an inner diameter approximately equal to or less than the outer profile of the collapsed balloon over the dam(s). The inner and outer sleeves are removed prior to use of the catheter.

Alternatively, the balloon protector may comprise a single compressive sleeve. This single compressive sleeve may be of any configuration described herein. A preferred embodiment of the single sleeve has a slit along the length thereof. Another preferred embodiment of the single sleeve has a helical slit along a predetermined length of the sleeve, defining a spiral cut region and a continuous tubular region. Yet another preferred embodiment has a spiral cut region and a continuous tubular region, the continuous tubular region comprising a dimpled region and a straight tubular region. The dimples may be round-like, spiral, triangular, oblong, longitudinal, circular (like tire treads) around the circumference or at an angle to the circumference, or combinations thereof. The dimples may also be of any other suitable configuration. In another alternative embodiment, the single sleeve may comprise a dimpled region extending along part of the single sleeve or the entire sleeve.

The present invention also provides a stent delivery system including a catheter having an expandable distal portion constructed and arranged for expanding the outer diameter of the catheter from a contracted state to an expanded state. The distal portion of the catheter may further comprise one or two dams (also referred to as enlarged portions, stops, bumpers, longitudinal motion preventers, or the like) and a balloon. A stent is positioned around the distal portion of the catheter. Where there is a single dam, the stent may be positioned either proximally or distally of the dam. In an embodiment having a single proximal dam, the stent is positioned distally of the proximal dam. In an embodiment having a single distal dam, the stent is positioned proximally of the distal dam. Where two spaced dams are present, the stent is positioned between the dams, i.e. distally of the proximal dam and proximally of the distal dam. The stent has a contracted condition, being sized in the contracted condition to closely surround the balloon (the balloon in such instance being folded or otherwise collapsed), and being expandable to an expanded condition. The stent delivery system further comprises a stent protector means comprising removable first and second sleeves. The first removable (inner) sleeve is positioned around the stent and between the dams, the inner sleeve being made of a lubricious material and further comprising a first end, a second end and an expansion slit extending therethrough. The slit may extend from end to end. Alternatively, the slit may extend along a predetermined length of the sleeve, the rest of the length of the sleeve comprising a continuous tube. The continuous tube may further comprise a dimpled region and a straight tubular region. The slit provides a variable inner diameter to ease sliding the sleeve over the balloon and stent. The second removable (outer) sleeve is positioned over the stent, first sleeve and dams, the outer sleeve having a constrictive relationship with the inner sleeve. The outer sleeve thereby provides an additional compressive force to reduce the profile of the stent and collapsed balloon. For example, the outer sleeve may have an inner diameter less than the outer diameter of the inner sleeve, whereby when compressed by the outer sleeve, the inner sleeve will have an inner diameter approximately equal to or less than the outer profile of the collapsed balloon over the dam(s). The stent protector means provides reduction of the profile of the compressed stent over the collapsed balloon.

Alternatively, the stent protector means may comprise a single compressive sleeve. This single compressive sleeve may be of any configuration described herein. A preferred embodiment of the single sleeve has a slit along the length thereof. Another preferred embodiment of the single sleeve has a helical slit along a predetermined length of the sleeve, defining a spiral cut region and a continuous tubular region. Yet another preferred embodiment has a spiral cut region and a continuous tubular region, the continuous tubular region comprising a dimpled region and a straight tubular region. The dimples may be round-like, spiral, triangular, oblong, longitudinal, circular (like tire treads) around the circumference or at an angle to the circumference, or combinations thereof. The dimples may also be of any other suitable configuration. In another alternative embodiment, the single sleeve may comprise a dimpled region extending along part of the single sleeve or the entire sleeve. The sleeve(s) are removed prior to use of the stent delivery system.

BRIEF DESCRIPTION OF THE FIGURES

FIG. 1 is a side view of a balloon catheter with a balloon protector according to the present invention having inner and outer sleeves, wherein the distal portion of the catheter thereof is in longitudinal section view which is enlarged relative to the proximal portion of said catheter;

FIG. 2 is an even more enlarged view in longitudinal cross-section of the distal portion of the catheter of FIG. 1 (indicated by dashed circle 2);

FIG. 3a is a perspective view of a balloon protector sleeve according to the present invention; FIG. 3b is a side view thereof;

FIG. 4a is a perspective view of an alternative balloon protector sleeve according to the present invention and FIG. 4b is a side partial section view of an alternative balloon protector sleeve according to the present invention;

FIG. 5 is an even more enlarged cross-section view taken along line 5-5 of FIG. 1;

FIGS. 6a-c are side views of alternative balloon protector sleeves according to the present invention;

FIG. 7 is a side section view of an alternative balloon protector sleeve according to the present invention;

FIG. 8 is a side view of a further alternative balloon protector sleeve according to the present invention;

FIGS. 9a-h and i are side views of further alternative balloon protector sleeves according to the present invention;

FIGS. 10a-d are perspective views of further alternative balloon protector sleeves according to the present invention;

FIG. 15 is a side view of an alternative balloon catheter with balloon protector according to the present invention, wherein the distal portion of the catheter thereof is in longitudinal section view which is enlarged relative to the proximal portion of said catheter;

FIG. 16 is an even more enlarged view in longitudinal cross-section of the distal portion of the catheter of FIG. 15 (indicated by dashed circle 16);

FIG. 17 is a side view of an alternative balloon catheter with balloon protector according to the present invention, wherein the distal portion of the catheter thereof is in longitudinal section view which is enlarged relative to the proximal portion of said catheter;

FIG. 18 is an even more enlarged view in longitudinal cross-section of the distal portion of the catheter of FIG. 17 (indicated by dashed circle 17);

FIG. 19 is a side view of a stent delivery system according to the present invention with stent protector according to the present invention, wherein the distal portion of the catheter thereof is in longitudinal section view which is enlarged relative to the proximal portion of said catheter;

FIG. 20 is an even more enlarged view in longitudinal cross-section of the distal portion of the stent delivery system of FIG. 19 (indicated by dashed circle 20);

FIG. 21 is a side view of an alternative stent delivery system with stent protector according to the present invention, wherein the distal portion of the catheter thereof is in longitudinal section view which is enlarged relative to the proximal portion of said catheter;

FIG. 22 is an even more enlarged view in longitudinal cross-section of the distal portion of the stent delivery system of FIG. 21 (indicated by dashed circle 22);

FIG. 25 is an enlarged cross-section view taken along line 25-25 of FIGS. 19, 21 and 23;

FIG. 26 is a perspective view of a stent protector sleeve according to the present invention;

FIG. 27a is a perspective view of an alternative stent protector sleeve according to the present invention, and FIG. 27b is a side partial section view of an alternative stent protector sleeve according to the present invention;

FIGS. 28a-c are side views of alternative balloon protector sleeves according to the present invention;

FIG. 29 is a side section view of an alternative stent protector sleeve according to the present invention;

FIG. 30 is a side view of a further alternative stent protector sleeve according to the present invention;

FIGS. 31a-h and i are side views of further alternative stent protector sleeves according to the present invention;

FIG. 33 is a side view of a stent delivery system with a stent protector according to the present invention, wherein the distal portion of the catheter thereof is in longitudinal section view which is enlarged relative to the proximal portion of said catheter;

FIG. 34 is a cross sectional view of the stent delivery system of claim, 33 taken along line 34-34; and FIG. 35 is a side view of a stent delivery system with a stent protector according to the present invention, wherein the distal portion of the catheter thereof is in longitudinal section view which is enlarged relative to the proximal portion of said catheter;

FIG. 36 is a cross sectional view of the stent delivery system of claim 35 taken along line 36-36;

FIGS. 37-42 are cross sectional views of a stent delivery system as in FIGS. 33 and 35, showing alternative configurations of a stent protector means thereof; and FIGS. 43-45 are schematic representations of means for expanding the expandable member of the balloon catheters and stent delivery systems of the present invention.

FIGS. 46-48 are side partial section views of alternative embodiments of a single sleeve balloon protector having a continuous tubular region and a region having a helical slit therein defining a spiral cut region;

FIG. 49 is a longitudinal section view of a balloon catheter with a balloon protector according to the present invention;

FIG. 50 is a perspective view of a single sleeve balloon protector according to the present invention, the balloon protector having a helical slit therein defining a spiral cut region, and a continuous tubular region further comprising a dimpled region and a straight tubular region;

FIG. 51 is a side cross sectional view of the balloon protector as in FIG. 50, taken along the longitudinal axis thereof;

FIG. 52 is a perspective view of a single sleeve balloon protector according to the present invention, the balloon protector having a helical slit therein defining a spiral cut region, and a continuous tubular region further comprising a dimpled region and a straight tubular region;

FIG. 53 is a side cross sectional view of the balloon protector as in FIG. 52, taken along the longitudinal axis thereof;

FIG. 54 is a perspective view of a single sleeve balloon protector according to the present invention, the balloon protector having a dimpled region;

FIG. 55 is a side cross sectional view of the balloon protector as in FIG. 54, taken along the longitudinal axis thereof; and FIG. 56 is a perspective view of a single sleeve balloon protector according to the present invention, the balloon protector having a dimpled region along the entire length thereof.

DESCRIPTION OF THE PREFERRED EMBODIMENTS

Figure 11:
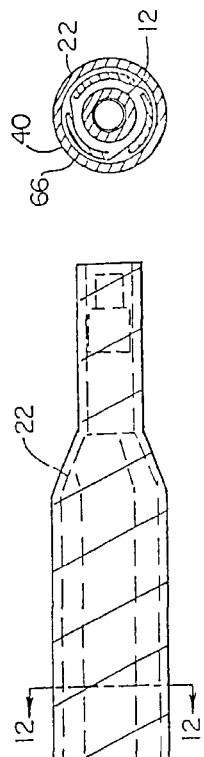
FIG. 11 is a side view of a balloon catheter with a balloon protector according to the present invention, wherein the distal portion of the catheter thereof is in longitudinal section view which is enlarged relative to the proximal portion of said catheter.

Referring to FIGS. 1-2, a medical device comprising a balloon catheter with a balloon protector according to the present invention is generally indicated at 10.

As shown at FIG. 1, catheter 12 has a shaft 13, a proximal portion 14 and a distal portion, indicated generally at 16, in longitudinal section view which is enlarged relative to the view of the proximal portion of said catheter. Distal portion 16 is fixed to catheter 12 by standard means known in the art. For instance, distal portion 16 may be bonded at its ends by adhesive to the catheter in an integral manner, or may be made one-piece with the catheter as is known in the art. Distal end portion 16 comprises balloon 22, which is constructed and arranged for expansion from a contracted state to an expanded state. FIG. 2 shows distal end portion 16 in an even more enlarged longitudinal cross-sectional view.

Balloon 22 may be of any length. For instance, balloon 22 may be about 15 mm long. This length, however, is for illustrative purposes only and is not meant to be limiting. Balloon 22 is shown in its contracted state in FIGS. 1-2. Balloon 22 may be folded or otherwise collapsed. Balloon 22 or any balloon set forth herein, may be made of a material which resiliently deforms under radial pressure. Examples of suitable materials are generally known in the art and include non-compliant, semi-compliant and compliant materials such as polyethylene (PE), nylon, polyether block amides (PEBAX), polyethylene terephthalate (PET), silicone, POC and the like. In addition, balloon 22 or any balloon set forth herein could be made of arnitel resin, such as Arnitel EM 740 sold by DSM Engineering Plastics, as set forth in U.S. Pat. No. 5,556,383, incorporated herein by reference.

In use, balloon 22 has a larger diameter which is obtained when the balloon 22 is expanded in the known manner. Catheter balloon 22 may be inflated by fluid (gas or liquid) from an inflation port extending from an inflation lumen contained in the catheter shaft 13 and opening into the balloon 22, or by other means, such as from fluid communication from a passageway or passageways formed between the outside of the catheter shaft and the membrane forming the balloon (schematically shown at FIGS. 43-45), depending on the design of the catheter. The passageway(s) could be either lead from the catheter shaft directly to the interior of the balloon (as shown at A in FIG. 43) or could lead to the exterior of the balloon (as shown at B of FIG. 44). The catheter may be associated with a source of fluid (gas or liquid) external to the catheter (schematically shown at FIG. 43), whereby the fluid is delivered to the balloon or expandable member by an inflation lumen located in the catheter shaft 13 and associated with the balloon 22. The details and mechanics of balloon inflation and specific overall catheter construction will vary according to the design of the catheter, and are known in the art per se. All of these variations are acceptable for use with the balloon catheters and stent delivery systems of the present invention.

Balloon catheter 10 further comprises balloon protector means, indicated generally at 26, comprising two removable sleeves. Two sleeves as described herein enhance compression of the balloon and provide a better profile. First removable (inner) protector sleeve 28 and second removable (outer) protector sleeve 40 may be made of any suitable low-friction material. Inner and outer sleeves 28,40 may be made of a low friction material which also will not stick to catheter 12 or balloon 22. A non-limiting example of a suitable material in is polytetrafluoroethylene. Inner sleeve 28 may be made of a lubricious plastic material or a material which is lubriciously coated.

In an alternative embodiment, outer balloon protector may be made of a shape memory metal or a shape memory polymer. The memory metal and memory polymer materials can be cast or molded and stretched to a larger size inner diameter. An outer balloon protector made of these materials provides the advantage of ease of insertion of the balloon therein since the balloon protector starts out with a larger diameter. Upon thermal or mechanical activation (such as by heating or twisting, for example) of the balloon protector of memory material, the balloon protector shrinks and tightens down, providing a reduced profile. Use of the inventive memory polymer balloon protector may require additional compression of the balloon before the set. A balloon protector made of a shape memory metal or shape memory polymer may be used with or without an inner sleeve.

As shown at FIGS. 1-2, first removable (inner) sleeve 28 is positioned around balloon 22. Inner sleeve 28 has a length less than or equal to the length of balloon 22 in its compressed state. Inner sleeve 28 comprises a straight tube with a first end 32, a second end 34 and a slit 36 therethrough (shown best at FIGS. 3a-b).

Slit 36 extends all the way along inner sleeve 28, from first end 32 to second end 34. Slit 36 is shown in FIGS. 3a-b as a longitudinal slit 37 extending the length of inner sleeve 28. An alternative embodiment of inner sleeve 28, as shown in FIGS. 4a and 4b, has a spiral slit 39. Optionally, inner sleeve 28 may have a tail 38 at its second end 34, to assist in its removal. Any outer sleeve, or a singular sleeve according to the present invention may be provided with the same configuration as shown at FIGS. 3-4 and 6-10.

Inner protector sleeve 28 is applied to catheter 12 over balloon 22 by moving inner sleeve 28 in a proximal direction from the distal end 16 of catheter 12, or alternatively by moving inner sleeve 28 in a distal direction from proximal end 14 of catheter 12. Inner sleeve 28 is gently urged over balloon 22 as sleeve is moved in a proximal direction relative to catheter 12. Slit 36 provides inner sleeve 28 with a variable inner diameter, which reduces the force required to apply inner sleeve 28 over balloon 22 by reducing friction between balloon 22 and the interior wall of inner sleeve 28. This ensures that balloon 22 and inner sleeve 28 will not be damaged during application or removal.

Referring to FIG. 5, an enlarged cross-sectional view, second removable (outer) sleeve 40 is positioned over balloon 22 and inner sleeve 28. Balloon 22 is shown in its contracted state in FIG. 5.

Outer sleeve 40 as shown in FIGS. 1-2 is a straight tube. Referring to FIGS. 6a-c, outer sleeve 40 may be a traditional balloon protector as shown at FIG. 6a having a main tubular body portion 42 with a proximal end 44 and a distal end 46 and having a flange 48 at its proximal end 44, a sleeve as shown at FIG. 6b with a flange 49 at its distal end 46, or as shown at FIG. 6c with flanges 48,49 at both proximal and distal ends 44,46. Sleeve 40 may also be a straight tube 50 with a tapered "lead-in" 52 as shown at FIG. 7, or the like. Other configurations will be readily apparent to those familiar with this art. The sleeves shown at FIGS. 6*a-c* can also be used as an outer sleeve with any suitable inner sleeve. The sleeve shown at FIG. 7 may also be used as a single sleeve balloon protector.

Referring to FIG. 8, an inner sleeve, outer sleeve or singular sleeve balloon protector of the present invention may also be provided in the form of a polymeric tube 60 with flared proximal end 62, flared distal end 64 and a longitudinal slit 37. This inventive balloon protector is unique in that the balloon protector can be removed from the catheter after the catheter has been prepped and loaded onto a guide wire. This allows the balloon protector to be peeled off the shaft, like peeling a banana. Such a construction allows a doctor to prep and introduce the guide wire into the catheter without touching the balloon.

A balloon protector according to the present invention may be a spiral sleeve 66 made of a polymeric material or a metal ribbon. It can also be formed by spiral cutting a tube to be the balloon protector, in a configuration as shown in FIGS. 9*a-h* and *j* and as shown at FIGS. 4*a-b*. This balloon protector conforms to diameter changes throughout the length of the collapsed balloon, and in a preferred embodiment has a pre-mounted inner diameter which is less than the outer diameter of the collapsed balloon to provide radial compression when applied on the balloon. The radial strength of the spiral sleeve is related to the material of which the sleeve is made, the pitch of the spiral, the wall thickness of the sleeve and the inner diameter of the sleeve. A preferred material for this balloon protector is LDPE. The spiral sleeve provides a device with a compressive force that has flexibility to conform to diameter changes of a collapsed balloon (a balloon which when expanded has a non-uniform diameter). The spiral sleeve 66 may be used alone as a single balloon protector, or as an inner sleeve with any suitable outer sleeve, for example, a sleeve with a longitudinal slit as shown at FIGS. 3 and 8. The spiral sleeve 66 may also be used as an outer sleeve with any suitable inner sleeve, for example, a sleeve with a longitudinal slit as shown at FIGS. 3 and 8.

FIGS. 9*a-h* and *i* show alternative embodiments of a spiral sleeve according to the present invention. FIGS. 9*a* and 9*b* show a spiral sleeve with a flare at one end, FIG. 9*a* showing a spiral sleeve with a proximal flare 48, and FIG. 9*b* showing a distal flare 49. FIG. 9*c* shows a spiral sleeve 66 with proximal and distal flares 48,49. Prior to use (in a premounted state) the spiral sleeves shown in FIGS. 9*a-c* have a substantially uniform outer diameter, inner diameter and wall thickness. FIG. 9*d* shows a spiral sleeve with proximal and distal flares 48,49. FIG. 9*e* shows a spiral sleeve with a distal flare. FIG. 9*f* shows a spiral sleeve with a proximal flare. Prior to use (in a premounted state) the spiral sleeves shown in FIGS. 9*d-f* have a substantially uniform outer diameter, a non-uniform, tapered inner non-uniform, tapered inner diameter and a non-uniform wall thickness. FIG. 9*g* shows a spiral sleeve with proximal and distal flares 48,49. FIG. 9*h* shows a spiral sleeve with a proximal flare 48. FIG. 9*i* shows a spiral sleeve with a distal flare 49. Prior to use (in a premounted state) FIGS. 9*g, h* and *i* have a non-uniform tapered inner and outer diameter, and a substantially uniform wall thickness.

A balloon may have various geometries over its length due to non-uniform areas. The spiral sleeve will conform around all portions and compress them. Following construction of a catheter, the balloon is formed and may be folded in multiple ways. For example, the balloon may be folded in a tri-fold manner.

Referring now to FIGS. 10*a-d*, a further embodiment of a balloon protector means according to the present invention may be provided in the form of a to coiled flat wire 70, spring wound without a gap between the coils, as shown at FIGS. 10*a* and 10*c*. Prior to thermal (such as by heating, for example), the coiled flat wire 70 may have a configuration as shown in FIGS. 10*b* and 10*d*. Upon thermal activation, the coiled flat wire 70 shrinks and tightens down, providing a reduced profile as shown in FIGS. 10*a* and 10*c*. Prior to mechanical activation, the coiled flat wire 70 may have a configuration as shown in FIGS. 10*a* and 10*c*. Upon mechanical activation (such as by twisting, for example), the coiled flat wire 70 is expanded to a configuration as shown in FIGS. 10*b* and 10*d*, allowing it to be applied on the catheter. Releasing the coiled flat wire 70 allows it to shrink and tighten down, providing a reduced profile as shown in FIGS. 10*a* and 10*c*. The coiled flat wire 70 may also be provided in a configuration as shown in FIGS. 4*a-b*. The embodiment shown at FIGS. 10*a-d* has an optional mechanical activation means 71. Mechanical activation means may be removable following mechanical activation or alternatively may be constructed and arranged for retention with coiled wire sleeve 70 and removal prior to use of catheter 12. The mechanical activation means may be of any suitable configuration, and is not intended to be limited hereby.

This outer balloon protector is a "one size fits all" which will accommodate all balloons, with or without stents in a delivery configuration. The advantages provided by this configuration is that it provides a "better squeeze" or higher externally applied compressive force than previous press-fit balloon protectors in the art. This configuration provides a compressive force that is variable along the length of the device, thereby providing a uniform compression amount along the entire length of a device which may or may not have a variable diameter. This balloon protector is easier to apply to a balloon than previous balloon protectors known in the art. Since the collapse column strength and friction forces are taken out of the assembly process, the production yield associated with catheters employing this balloon protector is improved.

Prior to placement of sleeves 28 and 40 on the catheter, outer sleeve 40 has an inner diameter less than the outer diameter of the inner sleeve 28. In a preferred embodiment, the inner diameter of outer protector sleeve 40 slightly smaller (about 0.001 inch smaller, for example) than the outer diameter of inner protector sleeve 28. This causes slit 36 to be closed when outer protector sleeve 40 is applied over inner protector sleeve 28, in addition to overall compression of inner protective sleeve 28. Inner sleeve 28 locates and holds balloon 22 while relatively tight outer sleeve 40 is pulled on. The lubricity of inner sleeve 28 reduces friction and enables outer sleeve 40 to be easily applied and removed from inner sleeve 28. Inner sleeve 28 provides the additional benefit of protecting the balloon 22 from damage.

As slit 36 is closed and forced together by outer protective sleeve 40, balloon 22 becomes more tightly wrapped and held. When outer sleeve 40 is in place, inner sleeve 28 is compressed by outer sleeve 40, and compressed inner sleeve 28 has an inner diameter approximately equal to the outer diameter of the compressed balloon. Outer sleeve 40 closes slit 36, and holds inner sleeve 28, and balloon 22 in place during sterilization and heat set profile forming (such as is disclosed in U.S. Pat. No. 5,342,307, incorporated herein by reference).

After both sleeves 28,40 are in place at distal end 16 of catheter 12, a heated sterilization cycle may be performed.

Balloon 22 will thereby by heat set into a further compressed form. The heat setting of balloon 22 provides a "memory" to balloon 22 so that when inner and outer sleeves 28,40 are removed prior to use, balloon 22 will remain in its compressed form. Even after inflation and deflation balloon 22 will tend to return to substantially the same shape as it had during the heat sterilization process. Therefore, small profiles can be achieved even after balloon inflation.

Inner and outer sleeves 28,40 are removed from catheter 12 prior to use thereof. Outer sleeve 40 is removed by pulling it off catheter 12. Inner sleeve 24 is removed in like manner, or pulled off using optional tail 38.

During delivery, the balloon catheter is advanced through and positioned in a patient's vasculature so that balloon is adjacent to the portion of the vessel where treatment is to take place. Balloon 22 is inflated and expanded to an enlarged diameter. Following use of balloon 22, balloon 22 is deflated so that catheter 12 may be removed.

Figure 12:
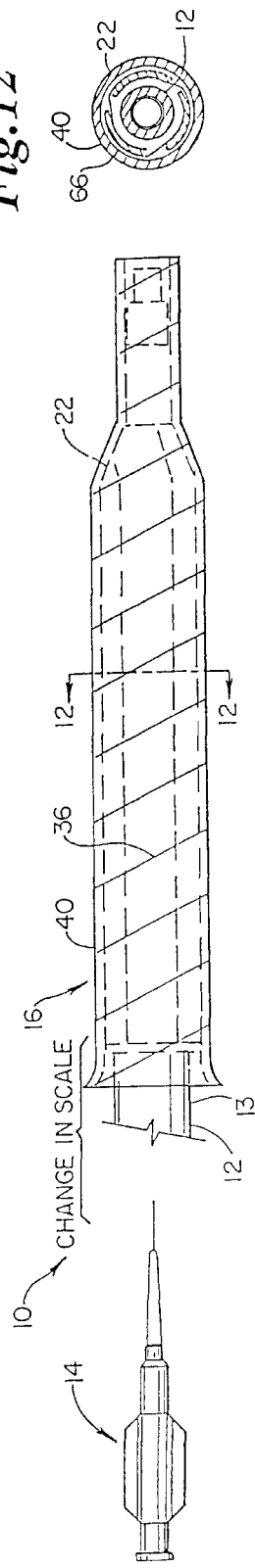
FIG. 12 is a side sectional view taken along line 12-12 of FIG. 11.

Referring now to FIGS. 11 and 12, wherein like features are designated by the same reference numerals, an alternative embodiment of a balloon catheter having a balloon protector according to the present invention is shown, wherein like features are designated by the same reference numerals as in FIG. 1. Balloon 22 is a folded balloon and the balloon protector 40 as shown is a single sleeve. Although any suitable sleeve according to the present invention may be used, the sleeve shown corresponds to that shown in FIG. 7.

Figure 13:
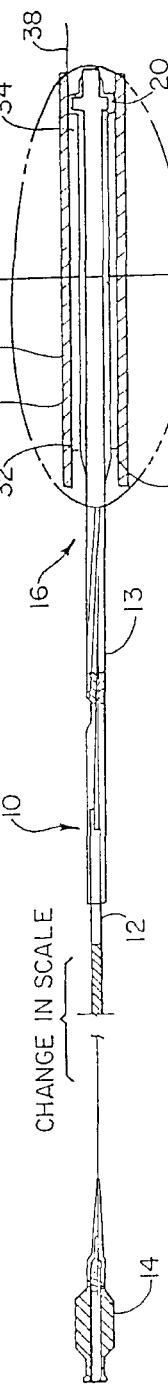
FIG. 13 is a side view of an alternative balloon catheter with balloon protector according to the present invention, wherein the distal portion of the catheter thereof is in longitudinal section view which is enlarged relative to the proximal portion of said catheter.
Figure 14:
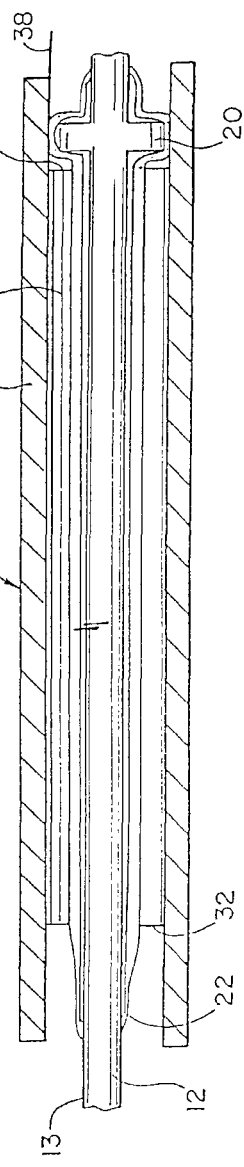
FIG. 14 is an even more enlarged view in longitudinal cross-section of the distal portion of the catheter of FIG. 13 (indicated by dashed circle 14)

Referring now to FIGS. 13-14, a balloon catheter with a balloon protector according to the present invention is generally indicated at 10.

As shown at FIG. 14, catheter 12 has a shaft 13, a proximal portion 14 and a distal portion, indicated generally at 16, in longitudinal section view which is enlarged relative to the view of the proximal portion of said catheter. Distal portion 16 is fixed to catheter 12 by standard means known in the art. For instance, distal portion 16 may be bonded at its ends by adhesive to the catheter in an integral manner, or may be made one-piece with the catheter as is known in the art. Distal end portion 16 comprises balloon 22, which is constructed and arranged for expansion from a contracted state to an expanded state. FIG. 14 shows distal end portion 16 in an even more enlarged longitudinal cross-sectional view. As shown in FIGS. 13-14, distal end portion 16 further comprises a distal dam (or stop) 20. Dam 20 may be conical or ring-like in shape, extending around the circumference of catheter 12. The majority of balloon 22 is located proximally of distal dam 20, a portion of balloon 22 covering and extending distally of distal dam 20.

As shown at FIGS. 15-16, which correspond respectively to FIGS. 13-14 and wherein like features are designated by the same reference numerals, catheter 12 may also have a single dam located at its proximal portion. In this embodiment, the majority of balloon 22 is located distally of proximal dam 18, a portion of the balloon 22 covering and extending proximally of proximal dam 18.

Referring to FIGS. 17-18, which correspond respectively to FIGS. 13-14, and wherein like features are designated by the same reference numerals, an alternative embodiment of balloon catheter 12 is shown wherein distal portion 16 further comprises proximal dam 18 spaced a predetermined distance from distal dam 20. Balloon 22 is located over and between dams 18,20.

Balloon 22 is shown in its contracted state in FIGS. 13-18. Balloon 22 may be folded or otherwise collapsed. Balloon 22 may be of any length. For instance, balloon 22 may be about 15 mm long in its contracted state. This length, however, is for illustrative purposes only and is not meant to be limiting.

Balloon 22 may be made of a material which resiliently deforms under radial pressure. Examples of suitable materials are generally known in the art and include non-compliant, semi-compliant and compliant materials such as polyethylene (PE), nylon, polyether block amides (PEBAX), polyethylene terephthalate (PET), silicone, POC and the like. In addition, balloon 22 could be made of arnitel resin, such as Arnitel EM 740 sold by DSM Engineering Plastics, as set forth in U.S. Pat. No. 5,556,383, incorporated herein by reference.

In use, balloon 22 has a larger diameter which is obtained when the balloon 22 is expanded in the known manner. Catheter balloon 22 may be inflated by fluid (gas or liquid) from an inflation port extending from a lumen contained in the catheter shaft 13 and opening into the balloon, or by other means, such as from fluid communication from a passageway formed between the outside of the catheter shaft and the membrane forming the balloon, depending on the design of the catheter. The catheter may be associated with a source of fluid (gas or liquid) external to the catheter, whereby the fluid is delivered to the balloon or expandable member by an inflation lumen located in the catheter shaft 13 and associated with the balloon 22. The details and mechanics of balloon inflation and specific overall catheter construction will vary according to the design of the catheter, and are known in the art per se. All of these variations are acceptable for use with this invention.

Balloon catheter 10 further comprises balloon protector means, indicated generally at 26, comprising two removable sleeves. Two sleeves as described herein enhance compression of the balloon and provide a better profile. In this embodiment, the two sleeves may provide compression of the balloon at or below the dam (or stop) profile. First removable (inner) protector sleeve 28 and second removable (outer) protector sleeve 40 may be made of any suitable low-friction material. Inner and outer sleeves 28,40 may be made of a low friction material which also will not stick to catheter 12 or balloon 22. A non-limiting example of such a material is polytetrafluoroethylene. Inner sleeve 28 may be made of a lubricious plastic material or a material which is lubriciously coated.

In an alternative embodiment, outer balloon protector may be made of a shape memory metal or a shape memory polymer. The memory metal and memory polymer materials can be cast or molded and stretched to a larger size inner diameter. An outer balloon protector made of these materials provides the advantage of ease of insertion of the balloon therein since the balloon protector starts out with a larger diameter. Upon thermal or mechanical activation (such as by heating or twisting, for example) of the balloon protector of memory material, the balloon protector shrinks and tightens down, providing a reduced profile. Use of the inventive memory polymer balloon protector may require additional compression of the balloon before the set. A balloon protector made of a shape memory metal or shape memory polymer may be used with or without an inner sleeve.

As shown at FIGS. 17-18, first removable (inner) sleeve 28 is positioned around balloon 22. Inner sleeve 28 has a length less than or equal to that of balloon 22 in its compressed state. Inner sleeve 28 comprises a straight tube with a first end 32, a second end 34 and a slit 36 therethrough.

Slit 36 extends all the way along inner sleeve 28, from first end 32 to second end 34. Slit 36 is shown in FIGS. 3a-b as a longitudinal slit 37 extending the length of inner sleeve 28. An alternative embodiment of inner sleeve 28, as shown in FIGS. 4a and 4b, has a spiral slit 39. Optionally, inner sleeve 28 may have a tail 38 at its second end 34, to assist in its removal. Any outer sleeve, or a singular sleeve according to the present invention may be provided with the same configuration as shown at FIGS. 3-4 and 6-10.

In the embodiment shown at FIGS. 13-18, inner protector sleeve 28 is applied to catheter 12 over balloon 22 by moving inner sleeve 28 in a proximal direction from the distal end 16 of catheter 12, or alternatively by moving inner sleeve 28 in a distal direction from the proximal end 14 of catheter 12. Inner sleeve 28 is gently urged over balloon 22 as sleeve is moved in a proximal direction relative to catheter 12.

Slit 36 provides inner sleeve 28 with a variable inner diameter, which reduces the force required to apply inner sleeve 28 over balloon 22 by reducing friction between balloon 22 and the interior wall of inner sleeve 28. This ensures that balloon 22 or inner sleeve 28 will not be damaged during application or removal.

Referring to FIG. 5, an enlarged cross-sectional view, second removable (outer) sleeve 40 is positioned over balloon 22 and inner sleeve 28. Balloon 22 is shown in its contracted state in FIG. 5. In the embodiment shown at FIGS. 17-18, outer sleeve extends over dams 18,20.

Outer sleeve 40 as shown in FIGS. 13-18 is a straight tube. Referring to FIGS. 6a-c, outer sleeve 40 may be a traditional balloon protector as shown at FIG. 6a having a main tubular body portion 42 with a proximal end 44 and a distal end 46, and having a flange 48 at its proximal end 44, as shown at FIG. 6b having a flange 49 at its distal end 46, or as shown at FIG. 6c having flanges 48,49 at proximal and distal ends 44,46. Outer sleeve may be a straight tube 50 with a tapered "lead-in" 52 as shown at FIG. 7. Other configurations will be readily apparent to those familiar with this art. The sleeves shown at FIGS. 6a-c can also be used as an outer sleeve with any suitable inner sleeve. The sleeve shown at FIG. 7 may also be used as a single sleeve balloon protector.

Referring to FIG. 8, an inner sleeve, outer sleeve or singular sleeve balloon protector of the present invention may also be provided in the form of a polymeric tube 60 with flared proximal end 62, flared distal end 64 and a longitudinal slit 37. This inventive balloon protector is unique in that the balloon protector can be removed from the catheter after the catheter has been prepped and loaded onto a guide wire. This allows the balloon protector to be peeled off the shaft, like peeling a banana. Such a construction allows a doctor to prep and introduce the guide wire into the catheter without touching the balloon.

A balloon protector according to the present invention may be a spiral sleeve made of a polymeric material or a metal ribbon. It can also be formed by spiral cutting a tube to be the balloon protector, in a configuration as shown in FIGS. 9a-c or in FIGS. 4a-b. This balloon protector conforms to diameter changes throughout the length of the collapsed balloon, and in a preferred embodiment has a pre-mounted inner diameter which is less than the outer diameter of the collapsed balloon to provide radial compression when applied on the balloon. The radial strength of the spiral sleeve is related to the material of which the sleeve is made, the pitch of the spiral, the wall thickness of the sleeve and the inner diameter of the sleeve. A preferred material for this balloon protector is LDPE. The spiral sleeve provides a device with a compressive force that has flexibility to conform to diameter changes of a collapsed balloon (a balloon which when expanded has a non-uniform diameter). The spiral sleeve 66 may be used alone as a single balloon protector, or as an inner sleeve with any suitable outer sleeve, for example, a sleeve with a longitudinal slit as shown at FIGS. 3 and 8. The spiral sleeve 66 may also be used as an outer sleeve with any suitable inner sleeve, for example, a sleeve with a longitudinal slit as shown at FIGS. 3 and 8.

A balloon may have various geometries over its length due to non-uniform areas. The spiral sleeve will conform around all portions and compress them. Following construction of a catheter, the balloon is formed and may be folded in multiple ways. For example, the balloon may be folded in a tri-fold manner.

Referring to FIGS. 10a-d, a further embodiment of an outer balloon protector according to the present invention may be provided in the form of a coiled flat wire 70, spring wound without a gap between the coils, as shown at FIGS. 10a and 10c. Prior to thermal or mechanical activation (such as by heating or twisting, for example, the coiled flat wire 70 may have a configuration as shown in FIGS. 10b and 10d. Upon thermal or mechanical activation, the coiled flat wire 70 shrinks and tightens down, providing a reduced profile as shown in FIGS. 10a and 10c. The embodiment shown at FIGS. 10a-d has an optional mechanical activation means 71. Mechanical activation means may be removable following mechanical activation or alternatively may be constructed and arranged for retention with coiled wire sleeve 70 and removal prior to use of catheter 12. The mechanical activation means may be of any suitable configuration, and is not intended to be limited hereby.

This outer balloon protector is a "one size fits all" which will accommodate all balloons, with or without stents in a delivery configuration. The advantage provided by this configuration is that it provides a "better squeeze" or higher externally applied compressive force than previous press-fit balloon protectors in the art. This configuration provides a compressive force that is variable along the length of the device, thereby providing a uniform compression amount along the entire length of a device which may or may not have a variable diameter. This balloon protector is easier to apply to a balloon than previous balloon protectors known in the art. Since the collapse column strength and friction forces are taken out of the assembly process, the production yield associated with catheters employing this balloon protector is improved.

Prior to mounting inner sleeve 28 and outer sleeve 40 on a catheter, outer sleeve 40 has an inner diameter less than the outer diameter of the inner sleeve 28. In a preferred embodiment, the inner diameter of outer protector sleeve 40 is slightly smaller (for example, about 0.001 inch smaller) than the outer diameter of inner protector sleeve 28. This causes slit 36 to be closed when outer protector sleeve 40 is applied over inner protector sleeve 28, in addition to overall compression of inner protective sleeve 28. Inner sleeve 28 locates and holds balloon 22 while relatively tight outer sleeve 40 is pulled on. The lubricity of inner sleeve 28 reduces friction and enables outer sleeve 40 to be easily applied and removed from inner sleeve 28. Inner sleeve 28 provides the additional benefit of protecting the balloon 22 from damage.

As slit 36 is closed and forced together by outer protective sleeve 40, balloon 22 becomes more tightly wrapped and held. When outer sleeve 40 is in place, inner sleeve 28 is compressed by outer sleeve 40, and compressed inner sleeve 28 has an inner diameter approximately equal to the combined diameter of the compressed balloon and the dam. Outer sleeve 40 closes slit 36, and holds inner sleeve 28, and balloon 22 in place during sterilization and heat set profile forming (such as is disclosed in U.S. Pat. No. 5,342,307).

After both sleeves 28,40 are in place at distal end 16 of catheter 12, a heated sterilization cycle may be performed. Balloon 22 will thereby by heat set into a further compressed form. The heat setting of balloon 22 provides a "memory" to balloon 22 so that when inner and outer sleeves 28,40 are removed prior to use, balloon 22 will remain in its compressed form. Even after inflation and deflation balloon 22 will tend to return to substantially the same shape as it had during the heat sterilization process. Therefore, small profiles can be achieved even after balloon inflation.

Inner and outer sleeves 28,40 are removed from catheter 12 prior to use thereof. Outer sleeve 40 is removed by pulling it off catheter 12. Inner sleeve 24 is removed in like manner, or pulled off using optional tail 38.

During delivery, the balloon catheter is advanced through and positioned in a patient's vasculature so that balloon is adjacent to the portion of the vessel where treatment is to take place. Balloon 22 is inflated and expanded to an enlarged diameter. Following use of balloon 22, balloon 22 is deflated so that catheter 12 may be removed.

Referring to FIGS. 19-20, a stent delivery system according to the present invention is indicated generally at 110. As shown at FIG. 20, stent delivery system 110 includes a catheter 112 having a shaft 113, a proximal portion 114 and a distal portion (indicated generally at 116) in longitudinal section view which is enlarged relative to the view of the proximal portion of said catheter. Distal portion 116 is fixed to catheter 112 by standard means known in the art. For instance, distal portion 116 may be bonded at its ends by adhesive to the catheter in an integral manner, or may be made one-piece with the catheter as is known in the art. Distal portion 116 is constructed and arranged for expansion of its outer diameter from a contracted state to an expanded state.

FIG. 20 shows distal end portion in an even more enlarged longitudinal cross-sectional view. As shown in FIG. 20, distal end portion 116 further comprises a distal dam (or stop) 120. Dam 120 may be conical or ring-like in shape, extending around the circumference of catheter 112. Balloon 122 is located proximally of distal dam 120.

As shown at FIGS. 21-22, which correspond respectively to FIGS. 19-20 and wherein like features are designated by the same reference numerals, catheter 112 may also have a single dam located at its proximal portion. In this embodiment, balloon 122 is located distally of proximal dam 118.

Figure 23:
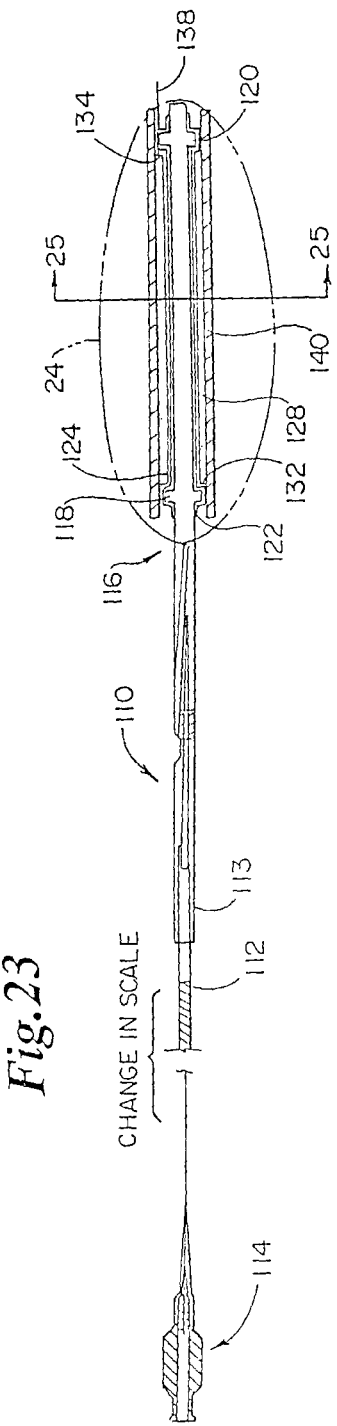
FIG. 23 is a side view of an alternative balloon catheter with balloon protector according to the present invention, wherein the distal portion of the catheter thereof is in longitudinal section view which is enlarged relative to the proximal portion of said catheter.
Figure 24:
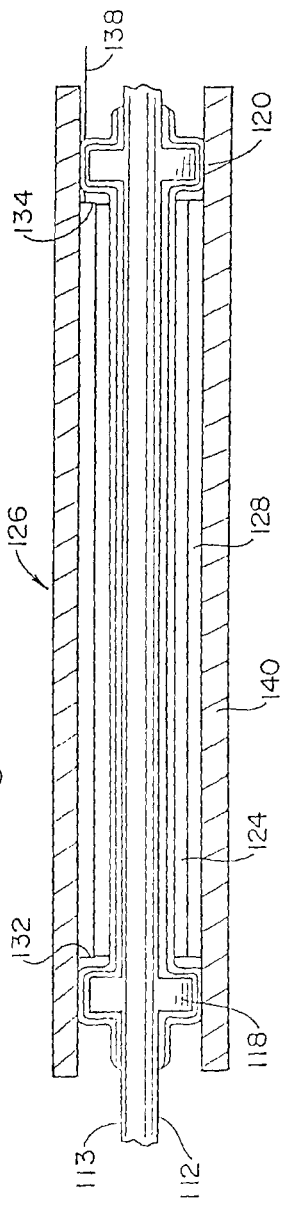
FIG. 24 is an even more enlarged view in longitudinal cross-section of the distal portion of the stent delivery system of FIG. 23 (indicated by dashed circle 24)

Referring to FIGS. 23-24, which correspond respectively to FIGS. 19-20, and wherein like features are designated by the same reference numerals, an alternative embodiment of balloon catheter 112 is shown wherein distal portion 116 comprises two dams, proximal dam 118 being spaced a predetermined distance from distal dam 120. Balloon 122 is located over and between dams 118,120.

Balloon is shown in its contracted state in FIGS. 19-24. Balloon 122 may be folded or otherwise collapsed. Balloon 122 may be made of a material which resiliently deforms under radial pressure. Examples of suitable materials are generally known in the art and include non-compliant, semi-compliant and compliant materials such as polyethylene (PE), nylon, polyether block amides (PEBAX), polyethylene terephthalate (PET), silicone, POC and the like. In addition, balloon 122 could be made of arnitel resin, such as Arnitel EM 740 sold by DSM Engineering Plastics, as set forth in U.S. Pat. No. 5,556,383, incorporated herein by reference.

Referring to FIG. 25, an enlarged cross-sectional view of a cross section taken along line 25-25 of FIGS. 19, 21 and 23, second removable (outer) sleeve 140 is positioned over balloon 122, stent 124 and inner sleeve 128. Balloon 122 is shown in its contracted state in FIG. 25. As shown in FIGS. 19-20, outer sleeve 140 extends over distal dam 120. As shown in FIGS. 21-22, outer sleeve 140 extends over proximal dam 118. In the embodiment shown at FIGS. 23-24, outer sleeve extends over dams 118,120.

Referring to FIGS. 19-24, catheter 112 has a shaft 113, a proximal portion 114 and a distal portion, indicated generally at 116, in longitudinal section view which is enlarged relative to the view of the proximal portion of said catheter. Distal portion 116 is fixed to catheter 112 by standard means known in the art. For instance, distal portion 116 may be bonded at its ends by adhesive to the catheter in an integral manner, or may be made one-piece with the catheter as is known in the art. Distal end portion 116 is constructed and arranged for expanding the outer diameter of the catheter from a contracted state to an expanded state.

As shown in FIGS. 19-24, stent 124 is positioned around the distal portion of catheter 112 (around balloon 122). As shown in FIGS. 19-20, stent 124 is located proximally of single distal dam 120. As shown in FIGS. 21-22, stent 124 is shown in a location distal to single proximal dam 118. As shown in FIGS. 23-24, stent 124 is positioned around the distal portion of catheter 112 (around balloon 122) between proximal dam 118 and distal dam 120.

Any self-expanding stent or balloon expandable stent may be used with this invention. Many are known in the art including plastic and metal stents. Some are more well known such as the stainless steel stent shown in U.S. Pat. No. 4,735,665; the wire stent shown in U.S. Pat. No. 4,950,227; another metal stent shown in European Patent Application EP0 707 837 A1 and that shown in U.S. Pat. No. 5,445,646. All of these patents are incorporated herein by reference. Also, shape memory metal stents may be used.

Stent 124 is typically about 15 mm long, while balloon 122 is roughly the same length. These dimensions, however, are merely representative for illustrative purposes only and are not meant to be limiting. In the embodiment shown at FIGS. 23-24 having spaced dams 118,120, the upper limit of the length of stent 124 is defined by the distance between dams 118,120.

Stent 124 has a contracted condition and an expanded condition, being sized in its contracted condition to closely surround the catheter. Stent 124 is fixed about balloon 122 by any suitable means as known in the art. For example, stent 124 may be gently crimped onto balloon 122 either by hand or with a tool such as a pliers or the like to be mounted for delivery.

Stent 124 has a larger expanded diameter which is obtained when the balloon 122 is expanded in the known manner. That is, stent 124 will be released from catheter 112 upon expansion of balloon 122 to be placed in a vessel. When balloon 122 is then deflated, removal of catheter 112 may be accomplished while leaving stent 124 in place.

Catheter balloon 122 may be inflated by fluid (gas or liquid) from an inflation port extending from a lumen contained in the catheter shaft 113 and opening into the balloon 122, or by other means, such as from fluid communication from a passageway formed between the outside of the catheter shaft 113 and the membrane forming the balloon, depending on the design of the catheter. The catheter may be associated with a source of fluid (gas or liquid) external to the catheter, whereby the fluid is delivered to the balloon or expandable member by an inflation lumen located in the catheter shaft 113 and associated with the balloon 122. The details and mechanics of balloon inflation and specific overall catheter construction will vary according to the design of the catheter, and are known in the art per se. All of these variations are acceptable for use with this invention.

Stent delivery system 110 further comprises stoat protector means, indicated generally at 126, comprising two removable sleeves. Two sleeves as described herein provide a better profile and enable compression of stent 124 below the dam (or stop) profile. First removable (inner) protector sleeve 128 and second removable (outer) protector sleeve 140 may be made of any suitable low-friction material. Inner and outer sleeves 128,140 may be made of a low friction material which also will not stick to catheter 112, balloon 122 or stent 124. An example of a such a material is polytetrafluoroethylene. Inner sleeve 128 may be made of a lubricious plastic material or a material which is lubriciously coated.

In alternative embodiment, the outer balloon protector according to the present invention may be made of a shape memory metal or a shape memory polymer. Such memory metal and memory polymer materials can be cast or molded and stretched to a larger size inner diameter. Such a stent protector provides the advantage of ease insertion of the catheter and stent since the stent protector starts out with a larger diameter. Upon thermal or mechanical activation (such as by heating or twisting, for example) of the stent protector of memory material, the stent protector shrinks and tightens down, providing a reduced profile. Use of the inventive memory polymer stent protector will require additional compression of the balloon and stent before the set. Such a stent protector may be used with or without an inner sleeve.

As shown at FIGS. 19-24, first removable (inner) sleeve 128 is positioned around stent 124. Inner sleeve 128 has a length approximately equal to that of stent 124 in its compressed state on catheter 112. Inner sleeve 128 comprises a straight tube with a first end 132, and a second end 134 and a slit 136 therethrough (as shown at FIG. 26).

Slit 136 extends all the way along inner sleeve 128, from first end 132 to second end 134. Slit 136 is shown in FIG. 26 as a longitudinal slit 137 extending the length of inner sleeve 128. An alternative embodiment of inner sleeve 128, as shown in FIGS. 27a and 27b, has a spiral slit 139. Optionally, inner sleeve 128 may have a tail 138 at its second end 134, to assist in its removal. Any outer sleeve, or a singular sleeve according to the present invention may be provided with the same configuration as shown at FIGS. 26-27 and 28-32.

In the embodiment shown at FIGS. 19-24, inner protector sleeve 128 may be applied to catheter 112 over balloon 122 and stent 124 by moving inner sleeve 128 in a proximal direction from the distal end 116 of catheter 112. Inner sleeve 128 is then gently urged over stent 124 as sleeve is moved in a proximal direction relative to catheter 112. Alternatively, inner protector sleeve 128 may be applied to catheter 112 over balloon 122 and stent 124 by moving inner sleeve 128 in a distal direction from the proximal end 114 of catheter 112, and inner sleeve 128 is then gently urged over stent 124 as sleeve is moved in a distal direction relative to catheter 112.

Slit 136 provides inner sleeve 128 with a variable inner diameter, which reduces the force required to apply inner sleeve 128 over stent 124 by reducing friction between stent 124 and the interior wall of inner sleeve 128, and allows inner sleeve 128 to fit over the dam(s). This ensures that balloon 122 or inner sleeve 128 will not be damaged by stent 124 during application or removal.

Outer sleeve 140 as shown in FIGS. 19-24 is a straight tube. Referring to FIGS. 28a-c, outer sleeve 140 may be a traditional balloon protector as shown at FIG. 28a having a main tubular body portion 142 with a proximal end 144 and a distal end 146 and having a flange 148 at its proximal end 144, as shown at FIG. 28b with a flange 149 at its distal end 146, or as shown at FIG. 28c with flanges 148,149 at both ends 144,146. Referring to FIG. 29, outer sleeve 140 may be a straight tube 150 with a tapered "lead-in" 152. Other configurations will be readily apparent to those familiar with this art. The sleeves shown at FIGS. 28a-c can also be used as an outer sleeve with any suitable inner sleeve. The sleeve shown at FIG. 29 may be used as a single sleeve balloon protector.

Referring to FIG. 30, an inner sleeve, outer sleeve or singular sleeve stent protector of the present invention may also be provided in the form of a polymeric tube 160 having flared proximal end 162, flared distal end 164 and longitudinal slit 137. This inventive stent protector is unique in that the stent protector can be removed from the catheter after the catheter has been prepped and loaded onto a guide wire. This allows the stent protector to be peeled off the shaft, like peeling a banana. Such a construction allows a doctor to prep and introduce the guide wire into the catheter without touching the preloaded stent.

Referring now to FIGS. 31a-h and *i*, a further alternative embodiment of a stent protector according to the present invention is a spiral sleeve 166 made of a polymeric material or a metal ribbon. The spiral sleeve can also be formed by spiral cutting a tube to be the stent protector, in a configuration as shown in FIGS. 31a-c and 27a-b. This stent protector conforms to diameter changes throughout the length of the stent and compressed balloon, and in a preferred embodiment has a pre-mounted inner diameter which is less than the outer diameter of the collapsed balloon to provide radial compression when applied on the balloon. The radial strength of the spiral sleeve is related to the material of which the sleeve is made, the pitch of the spiral, the wall thickness of the sleeve and the inner diameter of the sleeve. A preferred material for this balloon protector is LDPE. The spiral sleeve provides a device with a compressive force that has flexibility to conform to diameter changes of a collapsed balloon (a balloon which when expanded may have a non-uniform diameter) on which a stent is loaded. The spiral sleeve 166 may be used alone as a single stent protector, or as an inner sleeve with any suitable outer sleeve, for example, a sleeve with a longitudinal slit as shown at FIG. 26. The spiral sleeve 166 may also be used as an outer sleeve with any suitable inner sleeve, for example, a sleeve with a longitudinal slit as shown at FIG. 26.

FIGS. 31a-h and *i* show alternative embodiments of a spiral sleeve 166 according to the present invention. FIGS. 31a and 31b show a spiral sleeve with a flare at one end, FIG. 31a showing a spiral sleeve with a proximal flare 148, and FIG. 31b showing a distal flare 149. FIG. 31c shows a spiral sleeve 166 with proximal and distal flares 148,149. Prior to use (in a premounted state) the spiral sleeves shown in FIGS. 31a-c have a substantially uniform outer diameter, inner diameter and wall thickness. FIG. 31d shows a spiral sleeve with proximal and distal flares 148,149. FIG. 31e shows a spiral sleeve with a distal flare 149. FIG. 31f shows a spiral sleeve with a proximal flare 148. Prior to use (in a premounted state) the spiral sleeves shown in FIGS. 31d-f have a substantially uniform outer diameter, a non-uniform, tapered inner diameter and a non-uniform wall thickness. FIG. 31g shows a spiral sleeve with proximal and distal flares 148,149. FIG. 31h shows a spiral sleeve with a proximal flare 148. FIG. 31i shows a spiral sleeve with a distal flare 149. Prior to use (in a premounted state) FIGS. 31g, *h* and *i* have a non-uniform tapered inner and outer diameter, and a substantially uniform wall thickness.

This embodiment may be used not only with PTCA balloon catheters, but also with stent delivery systems comprising catheters on which a stent is loaded. The balloon may be folded in multiple ways. For example, the balloon may be folded in a tri-fold manner. A balloon may have various geometries over its length due to non-uniform areas. The stent may be crimped to the balloon. The spiral sleeve will conform around all portions and compress them.

Figure 32C:
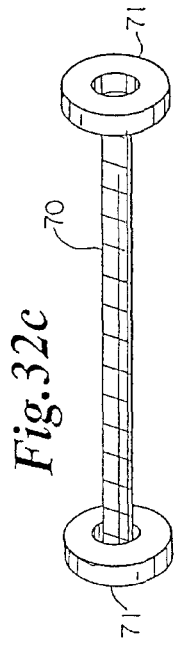
FIGS. 32a-d are perspective views of further alternative stent protector sleeves according to the present invention.
Figure 32D:
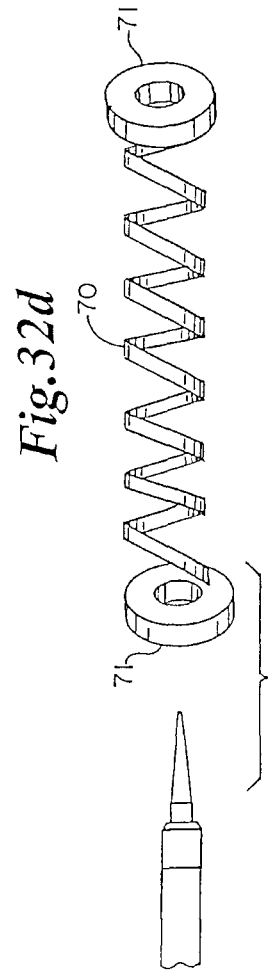
Figure 32A:
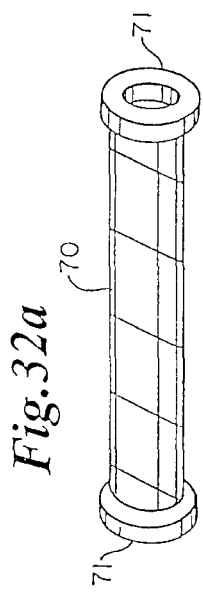
Figure 32B:
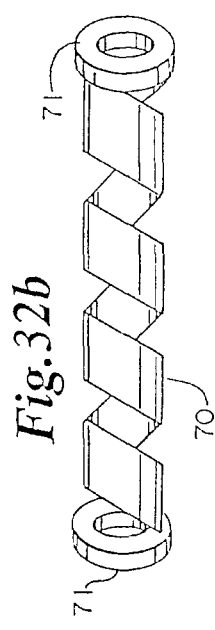

Referring now to FIGS. 32a-d, a further embodiment of an outer stent protector according to the present invention may be provided in the form of a coiled flat wire 170, spring wound without a gap between the coils, as shown at FIGS. 32a and 32c. Prior to thermal (such as by heating, for example), the coiled flat wire 170 may have a configuration as shown in FIGS. 32b and 32d. Upon thermal activation, the coiled flat wire 170 shrinks and tightens down, providing a reduced profile as shown in FIGS. 32a and 32c. Prior to mechanical activation, the coiled flat wire 170 may have a configuration as shown in FIGS. 32a and 32c. Upon mechanical activation (such as by twisting, for example), the coiled flat wire 170 is expanded to a configuration as shown in FIGS. 32b and 32d, allowing it to be applied on the catheter. Releasing the coiled flat wire 170 allows it to shrink and tighten down, providing a reduced profile as shown in FIGS. 32a and 32c. The coiled flat wire 170 may be provided in a configuration as shown at FIGS. 27a-b. The embodiment shown at FIGS. 32a-d has an optional mechanical activation means 171. Mechanical activation means may be removable following mechanical activation or alternatively may be constructed and arranged for retention with coiled wire sleeve 170 and removal prior to use of catheter 112. The mechanical activation means may be of any suitable configuration, and is not intended to be limited hereby.

This outer stent protector is a "one size fits all" which will accommodate all balloons, with or without stents in a delivery configuration. The advantages provided by this configuration is that it provides a "better squeeze" or higher externally applied compressive force than prior art stent protectors. This configuration provides a compressive force that is variable along the length of the device, thereby providing a uniform compression amount along the entire length of a device which may or may not have a variable diameter. This stent protector is easier to apply over a stent than previous stent protectors known in the art. Since the collapse column strength and friction forces are taken out of the assembly process, the production yield associated with stent delivery devices employing this stent protector is improved.

Prior to placement of inner sleeve and outer sleeve 140 on a catheter, outer sleeve 140 has an inner diameter less than the outer diameter of the inner sleeve 128. In a preferred embodiment, the inner diameter of outer protector sleeve 140 is slightly smaller (for example, about 0.001 inch smaller) than the outer diameter of inner protector sleeve 128. This causes slit 136 to be closed when outer protector sleeve 140 is applied over inner protector sleeve 128, in addition to overall compression of inner protective sleeve 128. Inner sleeve 128 locates and holds stent 124 while relatively tight outer sleeve 140 is pulled on. The lubricity of inner sleeve 128 reduces friction and enables outer sleeve 140 to be easily applied and removed from inner sleeve 128. Inner sleeve 128 provides the additional benefit of protecting the stent 124 from damage.

As slit 136 is closed and forced together by outer protective sleeve 140, stent 124 becomes more tightly wrapped and held. When outer sleeve 140 is in place, inner sleeve 128 is compressed by outer sleeve 140, and compressed inner sleeve 128 has an inner diameter approximately equal to the sum of the diameter of the compressed balloon and the dam(s). The stent delivery system of the present invention thereby enables compression of the stent below the dam profile. Outer sleeve 140 closes slit 136, and holds inner sleeve 128, stent 124 and balloon 122 in place during sterilization and/or heat set profile forming (such as is disclosed in U.S. Pat. No. 5,342,307).

After both sleeves 128,140 are in place at distal end 116 of catheter 112, a heated sterilization cycle may be performed. Balloon 122 will thereby be heat set into a further compressed form. The heat setting of balloon 122 provides a "memory" to balloon 122 so that when inner and outer sleeves 128,140 are removed prior to use, balloon 122 will remain in its compressed form. Even after inflation and deflation balloon 122 will tend to return to substantially the same shape as it had during the heat sterilization process. Therefore, small profiles can be achieved even after balloon inflation.

Inner and outer sleeves 128,140 are removed from stent delivery system 110 prior to use of the stent delivery system and deployment of stent 124 by expansion of the balloon. Outer sleeve 140 is removed by pulling it off catheter 112. Inner sleeve 124 is removed in like manner, or pulled off using optional tail 138.

During delivery, the balloon catheter is advanced through and positioned in a patient's vasculature so that stent 124 is adjacent to the portion of the vessel where treatment is to take place. Balloon 122 is inflated to expand stent 124 to an enlarged diameter. When stent 124 has reached the desired diameter, balloon 122 is deflated so that catheter 112 may be removed leaving stent 124 in place.

Referring now to FIGS. 33 and 35, alternative embodiments of a stent delivery system according to the present invention are shown generally at 210. Catheter 212 has a shaft 213, a proximal portion 214 and a distal portion, indicated generally at 216, shown in longitudinal section view which is enlarged relative to the view of the proximal portion of said catheter. Distal portion 216 is fixed to catheter 212 by standard means known in the art. For instance, distal portion 216 may be bonded at its ends by adhesive to the catheter in an integral manner, or may be made one-piece with the catheter as is known in the art. Distal portion 216 is constructed and arranged for expanding the outer diameter of the catheter from a contracted state to an expanded state. Distal portion 216 comprises a balloon 222, which has a proximal end 225, and a distal end 226. In the embodiments shown, proximal end 225 of balloon 222 is inwardly tapered and distal end 226 has an enlarged portion 227 which extends over distal dam 220. In FIGS. 34 and 36, cross sections respectively taken along line 34-34 of FIG. 33, and line 35-35 of FIG. 35, balloon 222 is shown to be a folded balloon in its compressed state.

As shown in FIGS. 33-34, stent 224 is positioned around the distal portion of catheter 212 (around balloon 222) between proximal end 225 and distal enlarged portion 227 thereof. This embodiment may be used with any stent protector means described herein. Inner sleeve 228 is shown, having approximately the same length as stent 224. Outer sleeve 240 is shown having a length greater than or equal to that of balloon 224.

As shown in FIGS. 35-36, stent 224 is positioned around balloon 222 between proximal end 225 and distal enlarged portion thereof. This embodiment may be used with any single sleeve stent protector according to the present invention. In a most preferred embodiment of the present invention as shown in FIGS. 35 and 36, the stent protector corresponds to that shown in FIGS. 27a-b or 31a-h and j.

Referring now to FIGS. 37-42, cross sectional views showing alternative configurations of a stent protector means indicated generally in FIGS. 33-40 at 226. In the embodiment shown in FIG. 37, a stent protector means is shown comprising a spiral sleeve 266, as shown in FIGS. 27a-b and 31a-h and j. In the embodiment shown in FIG. 38 a stent protector means is shown which comprises an inner sleeve 228 which is a spiral sleeve 266 as shown at FIGS. 27a-b and 31a-h and j, and an outer sleeve 240 of the type shown at FIGS. 28a-c and 29. The embodiment shown at FIG. 39 shows a stent protector means comprising an inner sleeve of the type having a longitudinal slit 237, as shown at FIGS. 26 and 30 and an outer sleeve which is a spiral sleeve 266 as shown at FIGS. 27a-b and 31a-h and j. The embodiment shown at FIG. 40 is a single sleeve stent protector of the type shown at FIGS. 26 and 39, which has a longitudinal slit 237. FIG. 41 shows an embodiment of a stent protector having an inner sleeve of the type shown at FIGS. 26 and 30, having a longitudinal slit 237 and an outer sleeve of the type shown at FIGS. 28*a-c* and 29. FIG. 42 shows a stent protector having an inner sleeve which is a spiral sleeve 266 as shown in FIGS. 27*a-b* and 31*a-h* and *j*, and an outer sleeve having a longitudinal slit 237 as shown in FIGS. 26 and 30.

FIGS. 46-48 are side partial section views of alternative embodiments of a single sleeve balloon or stent protector, indicated generally at 326, having a proximal end 328, a distal end 330, a continuous tubular region 332 and a spiral cut region 334 having a helical slit 336 therein. The embodiments shown at FIG. 46-48 are all single sleeve balloon protectors, each having a flare 338 at its proximal end 328, a helical slit 336 defining proximal spiral cut region 334, and a continuous tubular distal region 332. As shown at FIGS. 46-47, the tubular distal region 332 will extend proximally from the distal end 330 of the balloon protector 326 to the position of the balloon protector which covers the distal end of the most distal marker band, said distal marker band being located interior of balloon 322 and exterior of inner lumen 315 of catheter 312. The embodiment shown at FIG. 46 has a relatively shorter distal tubular region than that of the embodiment shown at FIG. 47. The length of the continuous tubular region will depend on the placement of the most distal marker band 317. As shown in FIG. 48, the proximal end of the distal tubular region may be located at any position from X to Y.

Referring now to FIGS. 49-55, an alternative embodiment of a balloon catheter having a balloon protector according to the present invention is shown. FIG. 49 is a longitudinal section view of the distal portion of a balloon catheter with a balloon protector according to the present invention, wherein the distal portion of the catheter thereof is in schematic longitudinal section view with a space between the balloon and balloon protector to show detail. The balloon protector actually closely surrounds the balloon. Balloon 422 is a folded or wrapped balloon and the balloon protector 440 as shown is a single sleeve. Although any suitable sleeve according to the present invention may be used, the sleeve shown corresponds to those shown in FIGS. 50-53.

As shown at FIG. 49, catheter 412 has a shaft 413, a proximal portion (not shown) and a distal portion, indicated generally at 416. Distal portion 416 is fixed to catheter 412 by standard means known in the art. For instance, distal portion 416 may be bonded at its ends by adhesive to the catheter in an integral manner, or may be made one-piece with the catheter as is known in the art. Distal end portion 416 comprises balloon 422, having a proximal end 423 and a distal end 425, balloon 422 being shown in a wrapped configuration around inner 427. At its proximal end 423, balloon 422 closely surrounds distal outer 429 at its distal end 431. Balloon 422 is constructed and arranged for expansion from a contracted state to an expanded state. Single sleeve balloon protector 426 has a proximal end 428, a distal end 430, and a dimpled region 440. This balloon protector may be of uniform diameter throughout its length, or tapered such that its diameter at distal end 430 is less than its diameter at proximal end 428. Balloon protector 426 will closely surround balloon 422.

FIGS. 50-53 are views of alternative embodiments of a single sleeve balloon or stent protector, indicated generally at 426, having a proximal end 428, a distal end 430, a continuous tubular region 432 and a spiral cut region 434 having a helical slit 436 therein. Each of the single sleeve balloon protectors shown at FIGS. 50-53 has a flare 438 at its proximal end 428, a helical slit 436 defining proximal spiral cut region 434, and a continuous tubular distal region 432. The inventive balloon protector as shown may optionally be provided without a proximal flare.

FIG. 50 is a perspective view of a single sleeve balloon protector according to the present invention, the balloon protector having a helical slit therein defining a spiral cut region, and a continuous tubular region further comprising a dimpled region 440 and a straight, smooth tubular region 442. FIG. 51 is a side cross sectional view of the balloon protector of FIG. 50.

FIG. 52 is a perspective view of a single sleeve balloon protector according to the present invention, the balloon protector having a helical slit therein defining a spiral cut region, and a continuous tubular region further comprising a dimpled region 440 that is a spiral dimpled region, and a smooth, straight tubular region 442. FIG. 53 is a side cross sectional view of the balloon protector of FIG. 52.

Alternatively, the balloon protector of the present invention may comprise a continuous tube having a spiral dimpled region 440 extending along part of its length, and a straight, smooth tubular region 442 extending along the remaining length as shown in FIGS. 54-55, or a spiral dimpled region 440 extending along its entire length, as shown in FIG. 56. The balloon protectors shown in FIGS. 54-56 may optionally be provided with a proximal flare as shown.

The balloon protector may be dimpled using a heat source. The dimples may be round-like, round or golf-ball like, spiral, triangular, oblong, longitudinal, circular (like tire treads) around the circumference or at an angle to the circumference, or combinations thereof. The dimples may also be of any other suitable configuration. Portions of the balloon protector may be "dimpled", as shown in FIGS. 50-55, or the entire balloon protector may be dimpled as shown in FIG. 56. The dimples may be provided on a partial length of the balloon protector, one quarter to one half the length, for example, or along the full length of the balloon protector. The dimples are generally not placed in areas corresponding to where marker bands are located.

The dimpling disclosed herein is an advantageous feature as it works the fold of the balloon and operates to break down fold edges, allowing smaller balloon protectors to fit over balloons. This yields reduced profiles and enables the catheter to track better and to better cross lesions.

Where a balloon protector is altered by the forming of multiple dimples in the material thereof, the dimples deform the inner diameter as well as the outer diameter and exterior surface. This is apparent in the cross sectional views. Dimples as disclosed herein may be formed on straight or tapered balloon protectors or in conjunction with a curved or bent product mandrel and any wrap style including "S", "trifold", or any fold such as quad, fix or six fold, for example.

The dimpled feature of the balloon protector, whether the dimples are spiral dimples or round, golf-ball-like dimples, will not only work the balloon cone down when sliding it over the balloon but will also work the balloon while it is removed, thereby enhancing profile reduction. The balloon protector may be twisted on or pushed on. Application by twisting on may lessen proximal bunching of the balloon.

This single sleeve balloon protector is a "one size fits all" which will accommodate all balloons, with or without stents in a delivery configuration. The advantage provided by this configuration is that it provides a "better squeeze" or higher externally applied compressive force than previous press-fit balloon protectors in the art. This configuration provides a compressive force that is variable along the length of the device, thereby providing a uniform compression amount along the entire length of a device which may or may not have a variable diameter. This balloon protector is easier to apply to a balloon than previous balloon protectors known in the art. Since the collapse column strength and friction forces are taken out of the assembly process, the production yield associated with catheters employing this balloon protector is improved.

Non limiting examples of suitable materials of which the single sleeve balloon or stent protectors of the present invention can be made are PTFE or LDPE. Other suitable materials are generally known in the art and include non-compliant, semi-compliant and compliant materials such as polyethylene (PE), nylon, polyether block amides (PEBAX), polyethylene terephthalate (PET), silicone, POC and the like. In addition, the balloon and stent protectors of the present invention could be made of arnitel resin, such as Arnitel EM 740 sold by DSM Engineering Plastics, as set forth in U.S. Pat. No. 5,556,383, incorporated herein by reference. In addition any sleeve set forth herein which may be made of a polymeric material may be made of one of these materials.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical device comprising:
   a catheter comprising a proximal portion, a distal portion, a shaft and an expandable member located at the distal portion, the catheter having an outer diameter, the expandable member having a length, said expandable member being constructed and arranged for expanding the outer diameter of said catheter from a contracted state to an expanded state; and
   a removable sleeve positioned around the entire length of the expandable member, said sleeve having a length and comprising a first end and a second end and having an outer diameter which is substantially uniform over the length of the sleeve and a variable inner diameter, the inner diameter increasing over the entire length of the sleeve,
   wherein the sleeve comprises a straight tube.

2. A medical device comprising:
   a catheter comprising a proximal portion, a distal portion, a shaft and an expandable member located at the distal portion, the catheter having an outer diameter, the expandable member having a length, said expandable member being constructed and arranged for expanding the outer diameter of said catheter from a contracted state to an expanded state; and
   a removable sleeve positioned around the entire length of the expandable member, said sleeve having a length and comprising a first end and a second end and having an outer diameter which is substantially uniform over the length of the sleeve and a variable inner diameter, the inner diameter increasing over the entire length of the sleeve,
   wherein the first end of the sleeve further comprises a proximal flare.

3. A medical device comprising:
   a catheter comprising a proximal portion, a distal portion, a shaft and an expandable member located at the distal portion, the catheter having an outer diameter, the expandable member having a length, said expandable member being constructed and arranged for expanding the outer diameter of said catheter from a contracted state to an expanded state; and
   a removable sleeve positioned around the entire length of the expandable member, said sleeve having a length and comprising a first end and a second end and having an outer diameter which is substantially uniform over the length of the sleeve and a variable inner diameter, the inner diameter increasing over the entire length of the sleeve,
   wherein said sleeve has a slit extending therethrough.

4. The medical device of claim 3 wherein the slit is a spiral slit extending in a helical manner from the first end of the sleeve to the second end of the sleeve.

* * * * *